US012636650B2

(12) United States Patent
Li

(10) Patent No.: US 12,636,650 B2
(45) Date of Patent: May 26, 2026

(54) DIGITAL PCR CHIP, AND DROPLET GENERATION SYSTEM AND DETECTION SYSTEM CONTAINING SAME

(71) Applicant: BEIJING ZHIYU BIOTECHNOLOGY LTD., Beijing (CN)

(72) Inventor: Ang Li, Beijing (CN)

(73) Assignee: BEIJING ZHIYU BIOTECHNOLOGY LTD., Beijing (CN)

( * ) Notice: Subject to any disclaimer, the term of this patent is extended or adjusted under 35 U.S.C. 154(b) by 1162 days.

(21) Appl. No.: 17/257,236

(22) PCT Filed: Apr. 19, 2019

(86) PCT No.: PCT/CN2019/083435
§ 371 (c)(1),
(2) Date: Apr. 15, 2021

(87) PCT Pub. No.: WO2020/007098
PCT Pub. Date: Jan. 9, 2020

(65) Prior Publication Data
US 2021/0229101 A1      Jul. 29, 2021

(30) Foreign Application Priority Data

Jul. 6, 2018   (CN) ......................... 201810737039.X
Jul. 6, 2018   (CN) ......................... 201810738786.5

(51) Int. Cl.
| | |
|---|---|
| *B01L 3/00* | (2006.01) |
| *B01L 3/02* | (2006.01) |
| *C12Q 1/686* | (2018.01) |

(52) U.S. Cl.
CPC ....... *B01L 3/502784* (2013.01); *B01L 3/0241* (2013.01); *B01L 3/50273* (2013.01);
(Continued)

(58) Field of Classification Search
CPC ....... G01N 1/4077; G01N 2035/00465; G01N 2035/0449; G01N 2035/00495;
(Continued)

(56) References Cited

U.S. PATENT DOCUMENTS

2009/0180930 A1*  7/2009  Aoki .................. G01N 35/1011
   422/63
2009/0221059 A1*  9/2009  Williams .............. B01L 3/5027
   422/400
(Continued)

FOREIGN PATENT DOCUMENTS

| CN | 104324769 A | 2/2015 |
|---|---|---|
| CN | 104324769 B | 2/2015 |

(Continued)

*Primary Examiner* — Dean Kwak
(74) *Attorney, Agent, or Firm* — Schmeiser, Olsen & Watts LLP

(57) ABSTRACT

A droplet generation system and detection method. The droplet generation system for digital PCR detection includes a PCR chip having a containing cavity; a microchannel having a first opening and a second opening for liquid to enter and exit; a rotation driving mechanism for driving the microchannel to reciprocating swing; and a fluid driving mechanism for driving the liquid to pass through the microchannel. An end of the microchannel where the first opening is located is capable of being inserted into the containing cavity and reciprocating swing in the containing cavity under the drive of the rotation driving mechanism.

18 Claims, 12 Drawing Sheets

(52) U.S. Cl.
CPC .............. *B01L 3/563* (2013.01); *C12Q 1/686*
(2013.01); *B01L 2200/0689* (2013.01); *B01L*
*2300/0816* (2013.01); *B01L 2300/168*
(2013.01); *B01L 2400/0487* (2013.01)

(58) Field of Classification Search
CPC ........... B01L 2400/0409; B01L 3/5021; B01L
3/502753; B01L 3/502784; B01L
3/50273; B01L 3/0241; B01L 3/563;
B01L 2200/0689; B01L 2300/0816; B01L
2300/168; B01L 2400/0487; B01L
2200/027; B01L 2200/0673; B01L
2300/0877; B01N 33/50; C12Q 1/686;
C12M 1/10; H02J 3/381
See application file for complete search history.

(56) References Cited

U.S. PATENT DOCUMENTS

2016/0289669 A1* 10/2016 Fan ................... B01L 3/502761
2019/0324050 A1* 10/2019 Williams .............. F16K 99/003

FOREIGN PATENT DOCUMENTS

| | | |
|---|---|---|
| CN | 104815709 | 8/2015 |
| CN | 105567560 | 5/2016 |
| CN | 107262170 | 10/2017 |
| CN | 208949317 | 6/2019 |
| WO | WO 03018753 | 3/2003 |

* cited by examiner

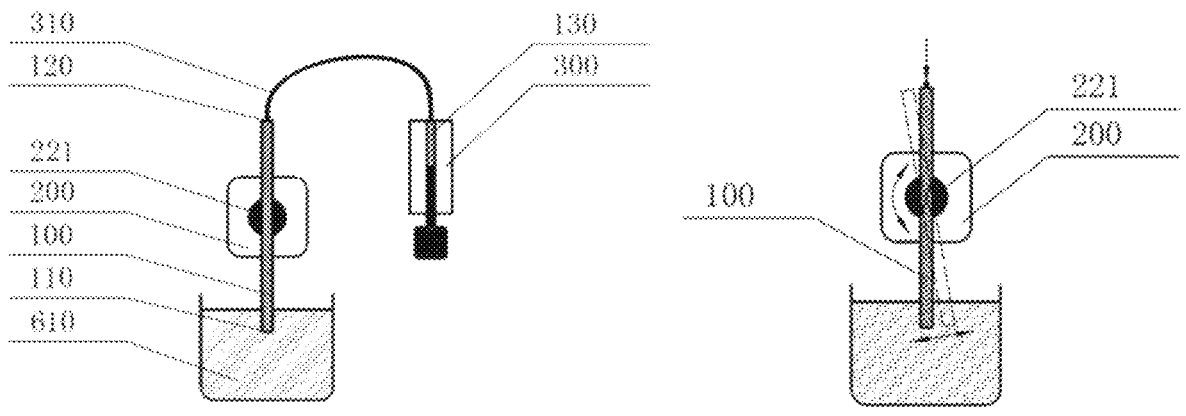
Figure 1                     Figure 2
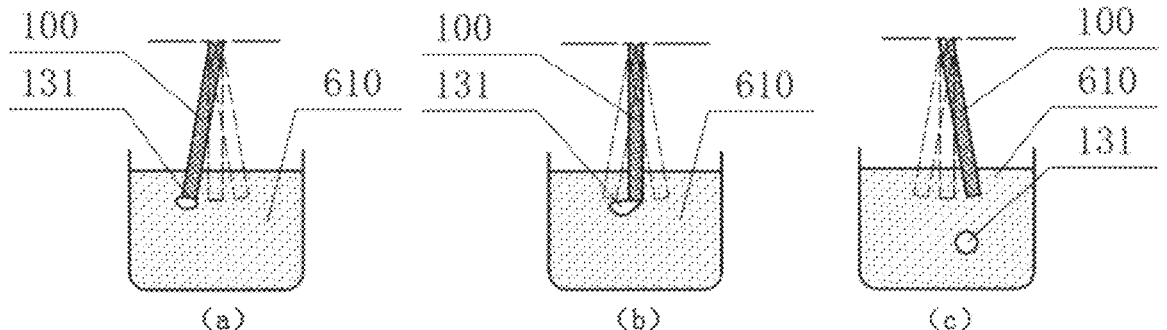
(a)               (b)               (c)
Figure 3
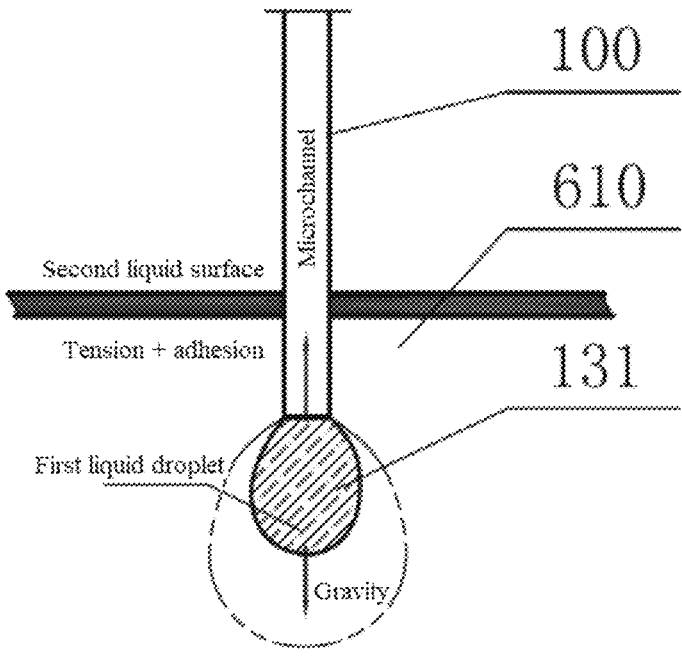
Figure 4

N–N

DIGITAL PCR CHIP, AND DROPLET GENERATION SYSTEM AND DETECTION SYSTEM CONTAINING SAME

CROSS-REFERENCE TO RELATED APPLICATIONS

This application is the U.S. National Phase under 35 U.S.C. § 371 of International Application PCT/CN2019/067514, filed Apr. 19, 2019, which is hereby incorporated by reference in its entirety, and which claims priority to Chinese Patent Application No. 201810738786.5, filed Jul. 6, 2018, and Chinese Patent Application No. 201810737039.X, filed Jul. 6, 2018.

TECHNICAL FIELD OF THE INVENTION

The present disclosure relates to a digital PCR chip, and a droplet generation system and detection system containing same.

BACKGROUND OF THE INVENTION

Polymerase chain reaction (PCR) technology is one of the most important tools in modern biology, which is widely used in medical diagnosis, personalized medicine, food inspection, genetically modified organism detection, pathogen identification, immune analysis, forensic science, etc. As the latest generation of PCR technology, digital PCR (dPCR) based on the development of microfluidic technology has a smaller reaction volume, faster reaction speed, lower system noise and higher sensitivity than traditional qPCR.

Droplet Digital PCR technology is a water-in-oil droplet technology based on a microfluidic chip, which encapsulates a single DNA molecule into a single droplet through a water-in-oil structure, and uses the inertness of oil to isolate DNA molecules from each other, each DNA molecule is confined to its own droplet to be amplified separately to avoid competition from other sequences. After completing the amplification of DNA molecules under suitable temperature conditions, by recording the total number of droplets and the number of droplets with fluorescent signals that can be detected, the accurate quantification of DNA copies can be achieved by using Poisson distribution algorithm.

It is one of the core technologies of micro-liquid operation to further divide the microliter level of liquid into a micro-reaction system with nanoliter or even picoliter volume. One of the main technical branches of micro-reaction system generation is the generation of emulsified micro-droplets. In recent years, a variety of micro-droplet generation technologies have been reported in the literature, such as membrane emulsification, spray emulsification, microfluidic chip, and microchannel injection/jetting. The recent Chinese invention patent ZL201410655191.5 and Chinese patent application CN104815709A further optimize the method of generating emulsified micro-droplets through microchannels. These methods of emulsifying micro-droplets have their own shortcomings in practical applications. The method of the Chinese invention patent ZL201410655191.5 uses the interface energy and fluid shear force when the trace liquid changes at the gas-liquid interface to overcome the surface tension and adhesion of the liquid at the outlet of the microchannel and make the droplets flowing out of the microchannel orifice can smoothly escape from the microchannel and form droplets of controllable size in the immiscible solution. However, in this method, the microchannel is required to cut and move up and down on the liquid surface, and high-precision positioning of the start and end positions of the microchannel relative to the liquid surface is required, which is very difficult to implement in engineering. The method of the Chinese patent application CN104815709A cuts off the injected immiscible solution to form droplets by the shear force generated by the circumferential or spiral constant motion of the microchannel in the liquid, however, this method is greatly affected by the changes of various system factors due to the size of the droplets produced by the microchannel (such as the viscosity of the liquid, the temperature of the environment, the speed of motion, the motion trajectory, etc.), and this deviation will accumulate as the number of droplets produced increases, so it is very difficult to control the uniformity of the volume and size of a large batch of droplets.

In the prior art, there are also some digital PCR chips that integrate droplet generation and droplet collection and storage, so that the droplets can be directly used for detection after collection. However, a chip with this structure is not easy to stably generate droplets or the stability and uniformity of the droplets are poor; the detection throughput of the chip is small, which cannot meet the requirements of clinical automation and high-throughput droplet analysis per unit area; in addition, this kind of chip has a complex structure, high processing precision requirements and high cost.

SUMMARY OF THE INVENTION

The present disclosure is aimed at providing an improved digital PCR chip to solve one or more deficiencies of the existing PCR chips.

The present disclosure further provides a digital PCR detection system and detection method based on the digital PCR chip, and a droplet generation system and a digital PCR detection method containing this digital PCR chip and used for digital PCR detection.

To achieve the above purpose, a technical solution employed by the present disclosure is: a digital PCR chip comprises a chip body having a droplet storage cavity, and a liquid inlet provided in the chip body, and the digital PCR chip further comprises a containing cavity standing on the chip body and being in communication with the liquid inlet, and a liquid outlet provided in the chip body; wherein the chip body further has a first channel enabling the liquid inlet to be in communication with the droplet storage cavity, and a second channel enabling the liquid outlet to be in communication with the droplet storage cavity, the first channel has a first internal pathway located inside the chip body, and the second channel has a second internal pathway located inside the chip body.

According to some preferred solutions of the present disclosure, the containing cavity extends upward from an upper surface of the chip body, and the liquid inlet is located at the bottom of the containing cavity.

According to some preferred solutions of the present disclosure, the containing cavity has a length of 2 to 30 mm, a width of 2 to 30 mm, and a height of 20 to 2000 μm.

According to some preferred solutions of the present disclosure, the containing cavity and the chip body are integrally formed, or the containing cavity are fixedly connected with the chip body.

According to some preferred solutions of the present disclosure, one end portion of the first channel is in communication with the droplet storage cavity; and/or, one end portion of the second channel is in communication with the droplet storage cavity.

According to some preferred solutions of the present disclosure, the first channel is located on one side of the droplet storage cavity; and/or, the second channel is located on one side of the droplet storage cavity.

According to some preferred solutions of the present disclosure, the first internal pathway and the second internal pathway are respectively arranged on two different sides of the droplet storage cavity.

According to some preferred solutions of the present disclosure, the droplet storage cavity has a first communication opening being in communication with the first channel and a second communication opening being in communication with the second channel, and the first communication opening and the second communication opening are respectively arranged on two opposite sides of the droplet storage cavity.

Further, the first communication opening is arranged facing the second communication opening.

According to a further implementation of the present disclosure, the droplet storage cavity has at least one arc chamfer, and the first communication opening is arranged at the arc chamfer.

According to a further implementation of the present disclosure, the droplet storage cavity is a polygon having arc chamfers; or, the droplet storage cavity is circular or elliptical.

According to a further implementation of the present disclosure, the droplet storage cavity is square or rectangular, the first communication opening and the second communication opening are respectively arranged at two opposite angles of the droplet storage cavity, the first internal pathway and the second internal pathway are respectively arranged on two opposite corners of the droplet storage cavity, and an end portion of the first communication opening is in communication with the first communication opening, and an end portion of the second communication opening is in communication with the second communication opening at end portions.

According to some preferred solutions of the present disclosure, part or the whole of the first channel and the second channel are curved.

Further, the first channel comprises at least one straight extension section and at least one arc extension section, and one end of the straight extension section is in communication with the liquid inlet, inner spaces of the at least one straight extension section and the at least one arc extension section form the first internal pathway.

According to a further implementation of the present disclosure, the first internal pathway is formed by inner spaces of one straight extension section and one arc extension section, the straight extension section is located outside the droplet storage cavity and is parallel to one side of the droplet storage cavity, and one end of the straight extension section is bent and extended toward the droplet storage cavity to form the arc extension section, and an end portion of the arc extension section away from the straight extension section is in communication with the droplet storage cavity.

As a preferred implementation, the droplet storage cavity, the first channel, and the second channel form a centrally symmetric structure.

According to some preferred solutions of the present disclosure, bottom surfaces of the first channel, the second channel and the droplet storage cavity are located at the same height.

According to some preferred solutions of the present disclosure, a height of the liquid inlet in the vertical direction is higher than that of the first channel, and/or, a height of the liquid outlet in the vertical direction is higher than that of the second channel.

According to the present disclosure, an inner diameter of the liquid inlet may be, for example, 4 mm-8 mm.

According to the present disclosure, the height of the liquid inlet may be, for example, 5 mm-15 mm.

According to the present disclosure, a height of the droplet storage cavity may be, for example, 50 mm-1000 µm. A length and width thereof are respectively, for example, 5 mm-30 mm.

According to the present disclosure, inner diameters of the first channel and the second channel may be respectively, for example, 4 mm-10 mm.

According to the present disclosure, a thickness of the chip body is 1-6 mm.

According to some preferred solutions of the present disclosure, the cross section of the droplet storage cavity is a square, and the side length of the square is 2 mm-30 mm; a height of the droplet storage cavity is 20-2000 µm.

According to some preferred solutions of the present disclosure, the chip further comprises a sealing cover for sealing the containing cavity.

Further, there is a plurality of containing cavities, and correspondingly, there is a plurality of sealing covers, and all the sealing covers are integrally arranged on an integral part.

According to some preferred solutions of the present disclosure, the digital PCR chip further comprises a drain pipe arranged on the chip body upright, and the drain pipe is in communication with the liquid outlet.

According to some preferred solutions of the present disclosure, the drain pipe extends upward from the upper surface of the chip body, which is integrally formed or fixedly connected with the chip body.

According to some preferred solutions of the present disclosure, a negative pressure connector for mating with an outlet of a negative pressure device is provided on the liquid outlet.

According to some preferred solutions of the present disclosure, the chip body is formed by superimposing a chip cover plate and a chip substrate in a thickness direction, the chip cover plate is a flat plate, a recess is provided on the chip substrate, and the flat plate and the recess are superimposed and compressed to form the droplet storage cavity, the first channel and the second channel.

According to a further implementation of the present disclosure, an opening of the recess faces downward, the chip substrate is located above the chip cover plate, and the chip cover plate is a transparent glass plate, a transparent PC plate, a transparent acrylic plate, a COP transparent plate or a black non-reflective plate.

According to another implementation of the present disclosure, an opening of the recess faces upward, the chip substrate is located below the chip cover plate, and the chip substrate and the chip cover plate are respectively made of plastic.

According to a preferred implementation of the present disclosure, the droplet storage cavity, the first channel, and the second channel jointly constitute a chip unit, and a plurality of chip units are arranged on the chip body.

According to a further implementation of the present disclosure, the chip body is rectangular, and the plurality of chip units is distributed along the length direction of the chip body.

The present disclosure further provides a digital PCR detection system, which comprises a digital PCR detection device, and further comprises the digital PCR chip as described above, and a negative pressure device for cooperating with the digital PCR chip, wherein the negative pressure device is used to generate negative pressure in the first channel, the droplet storage cavity and the second channel.

The present disclosure further provides a digital PCR detection method based on the digital PCR chip as described above or the digital PCR detection system as described above, which comprises a sample loading step of delivering droplets to the droplet storage cavity, and the sample loading step comprises:

filling the droplet storage cavity, the first channel, the second channel, and the containing cavity of the digital PCR chip with an oil phase;

injecting a water phase into the oil phase in the containing cavity by using a microchannel, and while injecting, reciprocating swinging the microchannel back and forth to form droplets in the containing cavity;

delivering droplets to the droplet storage cavity through the liquid inlet and the first channel.

According to some preferred solutions of the present disclosure, before injecting the water phase, fully filling the droplet storage cavity, the first channel, and the second channel with the oil phase.

According to some preferred solutions of the present disclosure, after filling the oil phase and before injecting the water phase, keeping both the liquid inlet and the liquid outlet in a sealed state, and letting the PCR chip to stand horizontally for more than 5 min.

According to some preferred solutions of the present disclosure, after starting to generate droplets or after completing droplet generation, switching on the negative pressure device to promote the discharge of the oil phase from the liquid outlet and to promote the flow of droplets to the droplet storage cavity.

The present disclosure further provides a droplet generation system comprising the digital PCR chip as described above and used for digital PCR detection, and the droplet generation system further comprises:

a microchannel having a first opening and a second opening for liquid to enter and exit;

a rotation driving mechanism for driving the microchannel to reciprocating swing; and a fluid driving mechanism for driving the liquid to pass through the microchannel;

wherein an end of the microchannel where the first opening is located is capable of being inserted into the containing cavity of the digital PCR chip and reciprocating swing back and forth in the containing cavity under the drive of the rotation driving mechanism.

According to some preferred solutions of the present disclosure, the droplet generation system further comprises a drain pipe arranged on the chip body upright, and the drain pipe is in communication with the liquid outlet.

Further, the drain pipe extends upward from an upper surface of the chip body, and is integrally formed or fixedly connected with the chip body. More further, a negative pressure connector for mating with an outlet of a negative pressure device is provided on the liquid outlet.

According to some preferred solutions of the present disclosure, the droplet storage cavity, the first channel, and the second channel jointly constitute a chip unit, and a plurality of chip units are arranged on the chip body.

According to some preferred solutions of the present disclosure, the reciprocating swing of the microchannel is horizontal swing; there is a liquid storage cavity with a volume of 10 μL to 100 μL between the first opening and the second opening of the microchannel.

According to some preferred solutions of the present disclosure, the fluid driving mechanism comprises an injector and a delivery pipe, a liquid inlet and outlet of the injector is in communication with the second opening of the microchannel through the delivery pipe, and an inner diameter of the delivery pipe is smaller than that of the microchannel. Preferably, the fluid driving mechanism further comprises an injector driving assembly for driving the injector to work. As a specific preferred implementation, the injector driving assembly comprises a lead screw nut driving mechanism or a rack and pinion driving mechanism.

According to some preferred solutions of the present disclosure, the droplet generation system further comprises a liquid storage tank with a liquid outlet, the liquid outlet of the liquid storage tank, the liquid inlet and outlet of the injector, and one end of the delivery pipe are connected via a three-way reversing valve.

According to some preferred solutions of the present disclosure, the driving mechanism is detachably connected with the microchannel. Further, the driving mechanism comprises a rotating motor, a rotating shaft, and a joint, an output end of the rotating motor is connected with the rotating shaft, the joint is fixedly connected to the rotating shaft in a direction perpendicular to an axis of the rotating shaft, and the microchannel is detachably mounted on the joint.

More further, the fluid driving mechanism comprises an injector and a delivery pipe, the joint is tubular and has a first liquid inlet and outlet and a second liquid inlet and outlet being in communication with each other internally, and one end of the delivery pipe is connected to the liquid inlet and outlet of the injector, the other end is connected with the first liquid inlet and outlet of the joint, and an end of the microchannel where the second opening is located is connected with the second liquid inlet and outlet of the joint; a plurality of joints are provided on one said rotating shaft, and one joint is connected with a plurality of micro-liquid pipes.

According to some preferred solutions of the present disclosure, the micro-droplet generation device further comprises a withdrawal mechanism for separating the microchannel from the joint. Further, an end of the microchannel where the second opening is located is sleeved on one end portion of the joint, and the withdrawal mechanism comprises a withdrawal plate slidably arranged on the joint and a withdrawal plate driving assembly driving the withdrawal plate to slide, and the microchannel is separated from the joint by the sliding of the withdrawal plate against the microchannel. Wherein, the withdrawal plate driving assembly is preferably a lead screw nut driving structure or a cylinder driving structure.

According to some preferred solutions of the present disclosure, the droplet generation system further comprises a base frame, the rotation driving mechanism is arranged on the base frame in a manner of being capable of sliding up and down, and the droplet generation system further comprises a longitudinal movement driving mechanism that drives the driving mechanism to slide.

According to some preferred solutions of the present disclosure, the droplet generation system further comprises a negative pressure device for cooperating with the PCR chip to generate negative pressure in the first channel, the droplet storage cavity and the second channel.

The present disclosure further provides a digital PCR detection method based on a droplet generation system as described above, the droplet is formed by mixing a water phase and an oil phase, the detection method comprises a sample loading step, and the sample loading step comprises:

filling the droplet storage cavity, the first channel, the second channel, and the containing cavity of the digital PCR chip with the oil phase;

inserting the first opening of the microchannel under a liquid surface of the oil phase in the containing cavity, initiating the rotating mechanism, driving the microchannel to reciprocating swing, and at the same time using the fluid driving mechanism and the microchannel to inject the water phase into the oil phase, to form droplets;

delivering droplets to the droplet storage cavity through the liquid inlet and the first channel.

According to some preferred solutions of the present disclosure, before injecting the water phase, fully filling the droplet storage cavity, the first channel, and the second channel with the oil phase.

According to some preferred solutions of the present disclosure, after filling the oil phase and before injecting the water phase, keeping both the liquid inlet and the liquid outlet in a sealed state, and letting the digital PCR chip to stand horizontally for more than 5 min.

According to some preferred solutions of the present disclosure, after starting to generate droplets, switching on the negative pressure device to promote the discharge of the oil phase from the liquid outlet and to promote the flow of droplets to the droplet storage cavity.

According to some preferred solutions of the present disclosure, a swing angle of the microchannel is $0.1°$ to $10°$; and a frequency of the reciprocating swing of the microchannel is 1 Hz to 1000 Hz.

According to the present disclosure, the "oil phase" and "water phase" have the general meanings in the art, and there is no particular limitation. The density of the oil phase is generally less than that of the water phase.

Due to the application of the above technical solutions, the present disclosure has the following advantages over the prior art: the structural design of the digital PCR chip of the present disclosure is based on a completely different design principle from the traditional digital PCR chip, and the containing cavity of the chip body of the digital PCR chip of the present disclosure constitutes a generation container for droplet generation, and after the droplets are generated in the containing cavity, they will be deposited on the liquid inlet by their own gravity, and then gradually enter the droplet storage cavity through the first channel. At the same time, in the present disclosure, through the structural design of the first channel, the second channel and the droplet storage cavity on the chip, the droplets maintain good stability during the delivery process and realize the uniform tiling of the droplets in the droplet storage cavity, thereby facilitating to obtain significantly more accurate detection results, and the digital PCR chip has significant advantages of simple structure and low cost. Further, based on the digital PCR chip structure and method of the present disclosure, it is also possible to achieve the multi-layer tiling of the droplets in the droplet storage cavity, which greatly improves the detection throughput, and meets the requirements of clinical automation and high-throughput droplet analysis per unit area.

The present disclosure further provides a new droplet generation system and generation thought at the same time. The droplet generation system integrates droplet formation and detection, not only can the droplets of uniform size be generated in large batches, but also the droplets can be directly used for detection, and the droplets can be evenly tiled in the droplet storage cavity, which is conducive to obtaining significantly more accurate detection results. The droplet generation system has obvious advantages of simple structure and low cost.

The digital PCR detection system and detection method of the present disclosure have many advantages such as high detection throughput and more accurate detection results.

BRIEF DESCRIPTION OF THE DRAWINGS

FIG. 1 is a schematic structure diagram of a micro-droplet generation device used in the present disclosure;

FIG. 2 is a schematic diagram of the reciprocating swing of the micro-droplet generation device used in the present disclosure;

FIG. 3 is a schematic diagram of micro-droplet generation of the micro-droplet generation device used in the present disclosure;

FIG. 4 is a schematic diagram of a situation where the microchannel is not connected to any vibration motor in the prior art;

DETAILED DESCRIPTION OF EXEMPLARY EMBODIMENTS

Figures 5, 6, 7, 8:
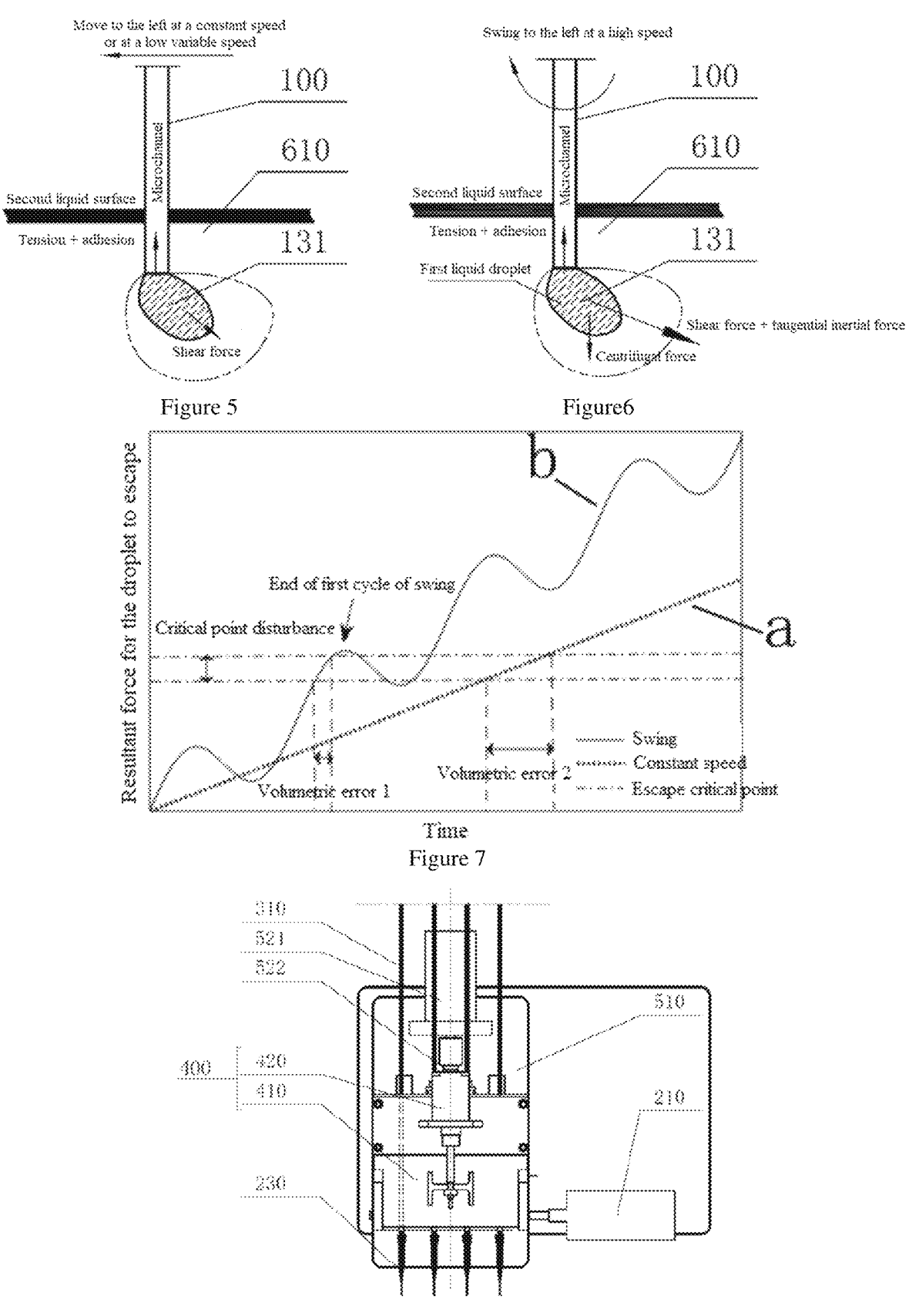
FIG. 5 is a schematic diagram of a situation where a microchannel is fixed on a vibration motor that can produce uniform linear motion in the prior art.
FIG. 6 is a schematic diagram of a situation where a microchannel is fixed on one rotation driving mechanism in the micro-droplet generation device used in the present disclosure.
FIG. 7 is a schematic diagram of analysis of related factors affecting the generation of micro-droplets.
FIG. 8 is a front view of an embodiment of a micro-droplet generation device.

In the following, the technical solution of the present disclosure is further described combining with the accompanying drawings and specific embodiments.

Firstly, the specific structure and working principle of the micro-droplet generation device used in the present disclosure will be described in detail combining the embodiments and the drawings. It should be understood that the specific embodiments described here are only used to explain the present disclosure, not to limit the present disclosure.

The present disclosure further provides a new droplet generation system and generation thought. The droplet generation system integrates droplet formation and detection. The basic configuration of the droplet generation system provided by the present disclosure comprises a microchannel, a rotation driving mechanism and a PCR chip, and the components other than the PCR chip are collectively referred to as a droplet generation device in the present disclosure. In the droplet generation system of the present disclosure, not only can the droplets of uniform size be generated in large batches, but also the droplets can be directly used for detection.

As shown in FIG. 1, it illustrates a microchannel 100, a rotation driving mechanism 200, and the like of the droplet generation system, the microchannel 100 has a first opening 110 for outputting a first liquid 130, and the rotation driving mechanism 200 is used to drive the microchannel 100 to reciprocating swing horizontally. As shown in FIG. 2, the rotation driving mechanism 200 drives the microchannel 100 to reciprocating swing around a center of rotation 221, so that the first opening 110 of the microchannel 100 also reciprocating swings, thereby generating micro-droplets 131 under the liquid surface of a second liquid 610.

As shown in FIG. 1, in order to enable the first opening 110 of the microchannel 100 to continuously generate micro-droplets 131, the micro-droplet generation device further comprises a fluid driving mechanism 300 in communication with the second opening 120 of the microchannel 100 via a delivery pipe 310. The second opening 120 of the microchannel 100 is in communication with the first opening 110, the fluid driving mechanism 300 can apply a stable driving force to the microchannel 100 through the delivery pipe 310, so that the first liquid 130 in the microchannel 100 can stably and continuously flow out of the first opening 110 and generates micro-droplets 131.

The droplet generation method provided by the present disclosure is a very complicated dynamic process, and there are many factors that affect the volume of generated droplets. The main factors are: the surface tension of the droplet (related to the opening area of the microchannel, and the difference in surface energy between the first and second liquid), the adhesion between the opening of the microchannel and the droplet (affected by the size and surface properties of the pipe opening); shear force (determined by the viscosity of the second liquid, the movement speed of the microchannel and the surface area of the droplet), centrifugal force (related to the mass of the droplet, the radial acceleration of the swing of the microchannel), and the tangential inertial force (being proportional to the swing tangential acceleration of the microchannel and the mass of the droplet). Centrifugal force is essentially radial inertial force.

As shown in FIG. 3, due to the first opening 110 of the microchannel 100 generates a rotational movement under the drive of the rotation driving mechanism 200, under the combined action of the shear force determined by the viscosity of the second liquid 610, the moving speed of the orifice of the first opening 110 of the microchannel 100, and the surface area of the micro-droplet 131, the centrifugal force related to the mass of the micro-droplet 131 and the swinging radial acceleration of the orifice of the first opening 110 of the microchannel 100, and the tangential inertial force proportional to the swinging tangential acceleration of the orifice of the first opening 110 of the microchannel 100 and the mass of the micro-droplet 131, the micro-droplet 131 formed at the orifice of the first opening 110 of the microchannel 100 from the first liquid 130 in the microchannel 100 escapes from the orifice of the first opening 110 of the microchannel 100 under the liquid surface of the second liquid 610.

The following will compare and analyze the reciprocating swing mode of the micro-droplet generation device used in the present disclosure (refer to FIGS. 6-7) and other methods (refer to FIGS. 4-5) to illustrate the unique technical effects obtained by the present disclosure. It is important to point out that all the following analyses take a droplet of the first liquid 130 flowing out of the microchannel as independent objects for force analysis, and the dotted frame in FIGS. 4-7 indicates that the droplet of the first liquid 130 is an independent system.

FIG. 4 is a schematic diagram of a situation where the microchannel is not connected to any vibration motor in the prior art. In the prior art, when the fluid driving device continuously injects the first liquid 130 into the second liquid 610 through the microchannel 100 at a constant speed, the droplet will gradually keep growing. Because the volume of the liquid is not compressible, the volume of the droplet will increase at a constant speed under the condition of constant injection. What acts on the droplet is the surface tension and adhesion to keep the droplet from escaping, and also downward gravity. When the droplet grows to a critical volume (refer to the volume shown by the dividing line in FIG. 4), the applied gravity overcomes surface tension and adhesion force to escape. Because the droplet must grow to the microliter level before gravity can overcome the tension and adhesion, this method cannot produce micro-droplets characterized by nanoliters.

FIG. 5 is a schematic diagram of a situation where a microchannel is fixed on a vibration motor that can produce uniform linear motion in the prior art. As shown in FIG. 5, in the prior art, when the fluid driving device continuously injects the first liquid 130 into the second liquid 610 through the microchannel 100 at a constant speed, the droplet will gradually keep growing. Because the volume of the liquid is not compressible, the volume of the droplet will increase at a constant speed under the condition of constant injection. The difference from the situation shown in FIG. 4 is that a linear motor is turned on at the same time to drive the microchannel 100 to move linearly to the left at a constant speed. Then, the force conditions the droplet is subjected to is shown in FIG. 5, because the droplet moves relative to the second liquid 610 and is subjected to a rightward shear force, the shear force is positively related to the speed and surface area of the droplet. Therefore, in the case of uniform speed, this force increases as the droplet volume increases. Gravity is much smaller than shear force and is thus ignored. In a certain critical volume (refer to the dividing line shown in FIG. 5), when the shear force overcomes the surface tension and adhesion, it is the moment when the droplet escapes from the mouth of the microchannel. Because of the fluctuation of the environment and the system, this critical volume will be disturbed up and down, which is the main factor causing the uneven droplet size (refer to the dotted line a in FIG. 7). Under this kind of movement at a constant speed, an error caused by this disturbance is very large (this problem exists in the prior art such as the microchannel droplet generation technology in FIG. 4 and the prior patent mentioned in the background section).

FIG. 6 is a schematic diagram of a situation where a microchannel is fixed on one rotation driving mechanism in the micro-droplet generation device of the present disclosure. As shown in FIG. 6, when the fluid driving device continuously injects the first liquid 130 into the second liquid 610 through the microchannel 100 at a constant speed, through the high-frequency swing, the speed change of the microchannel 100 has a high-frequency modulation, so that the resultant force received by the droplet also has a high-frequency modulation. The resultant force to escape is a combination of shear force, centrifugal force and tangential inertial force. When there is a disturbance at the critical point, this escape force changing at the high frequency is sufficient to break through the critical point disturbance in a very short time, thereby the volume error caused by the disturbance is minimized (because the volume of the droplet grows uniformly under the drive of the fluid driving device, the less time required to break through the critical disturbance means the small volume error). As shown in FIG. 7, it can be clearly seen that under the same critical disturbance, the volume error 1 generated by the swing of the microchannel fixed on a motor capable of reciprocating swinging is much smaller than the volume error 2 generated by a constant speed.

Figure 9:
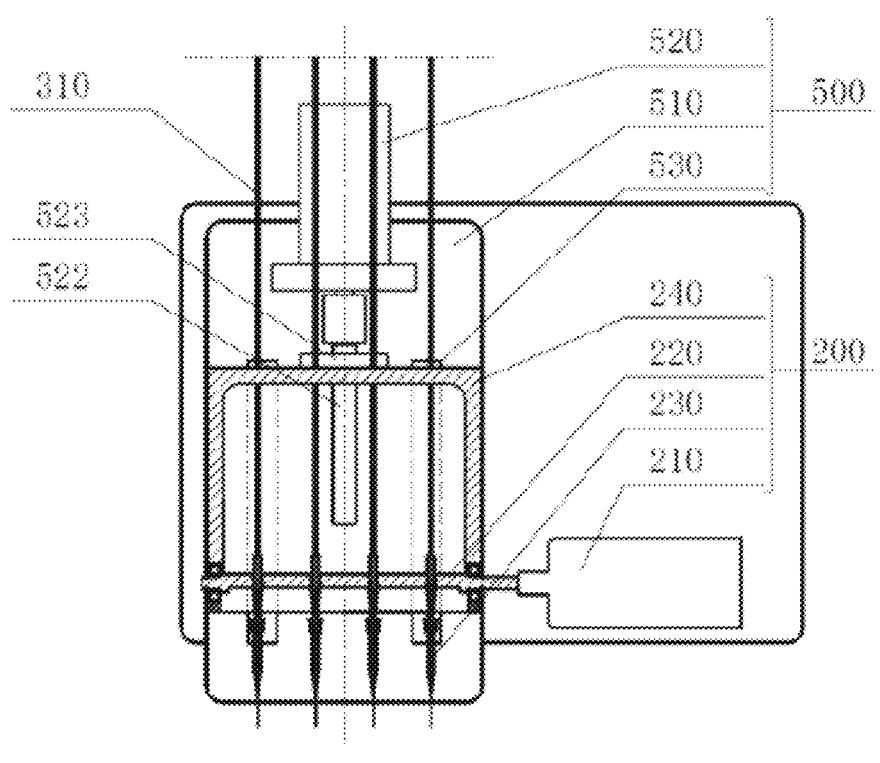
FIG. 9 is a front cross-sectional view of the micro-droplet generation device of one embodiment.
Figure 10:
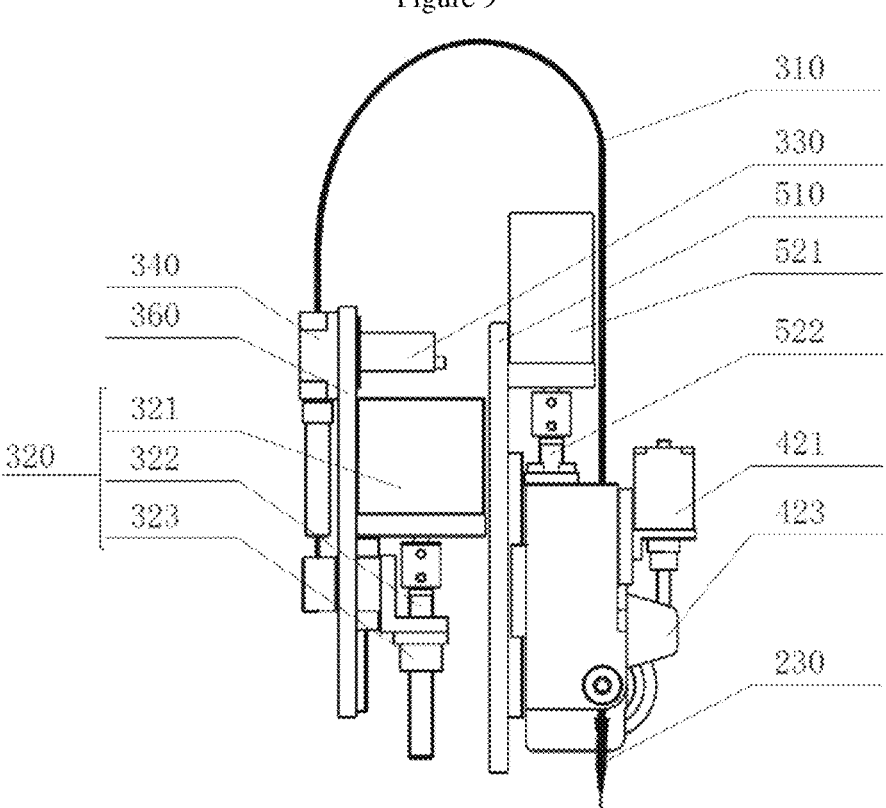
FIG. 10 is a left view of the micro-droplet generation device of one embodiment.

As shown in FIG. 8, FIG. 9 and FIG. 10, as a preferred implementation, the rotation driving mechanism 200 in the droplet generation device of the present disclosure comprises a rotating motor 210, a rotating shaft 220, and a joint 230, an output end of the rotating motor 210 is connected with the rotating shaft 220, the joint 230 is fixedly connected to the rotating shaft 220 in a direction perpendicular to the axis of the rotating shaft 220, and the microchannel 100 is mounted on the joint 230. The rotating motor 210 can drive the rotating shaft 220 and the joint 230 to rotate and swing around the axis of the rotating shaft 220 as a center, so as to drive the microchannel 100 to reciprocating swing. The rotation driving mechanism 200 in the droplet generation device of the present disclosure can also adopt other rotation driving devices, such as a swing cylinder, a rotating electromagnet, and the like.

Figure 13:
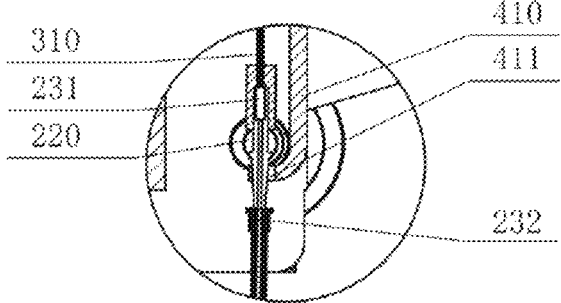
FIG. 13 is a partial enlarged view of Position C in FIG. 12.

In this implementation, the microchannel 100 has a tubular structure with openings at both ends, and in order to facilitate the assembly of the microchannel 100, the joint 230 is also tubular, combining with FIG. 13, the tubular joint 230 has a third opening 231 and a fourth opening 232 being internally in communicating with each other, the delivery pipe 310 is connected to the third opening 231, and the second opening 120 of the microchannel 100 is connected to the fourth opening 232. The fluid driving force output by the fluid driving mechanism 300 can be stably applied inside the microchannel 100 through the delivery pipe 310 and the joint 230, so that the first liquid 130 in the microchannel 100 can stably and continuously flow out of the first opening 110 and generate micro-droplets 131.

Figure 12:
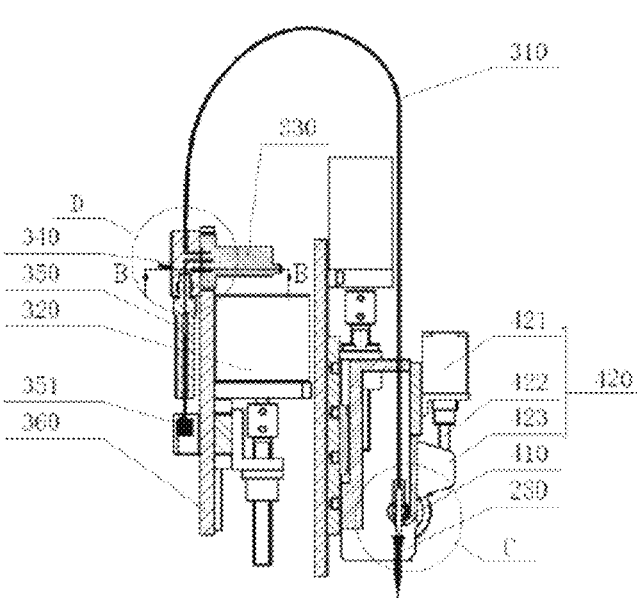
FIG. 12 is a cross-sectional view along A-A in FIG. 11.

Since the micro-droplet generation device of the present disclosure can be used in the field of biological detection, and in order to avoid cross-contamination of biological materials, the microchannel 100 is usually single-use, it is necessary to detach the microchannel 100 from the joint 230 after each use; in order to improve the disassembly efficiency, the micro-droplet generation device of the present disclosure further comprises a withdrawal mechanism 400, as shown in conjunction with FIG. 12 and FIG. 13, the withdrawal mechanism 400 comprises a withdrawal plate 410 and a withdrawal plate driving assembly 420, a withdrawal hole 411 is opened on the withdrawal plate 410, and the withdrawal hole 411 is sleeved outside the joint 230, the second opening 120 of the microchannel 100 is sleeved outside the fourth opening 232 and is opposite to the withdrawal plate 410, and the withdrawal plate driving assembly 420 is used to drive the withdrawal plate 410 to move towards the microchannel 100; when the withdrawal plate 410 pushes against the second opening 120 of the microchannel 100, it applies squeezing force to the microchannel 100 to detach it from the joint 230; if the withdrawal plate 410 continues to move, the microchannel 100 will be pushed out of the joint 230, and after that, the withdrawal plate drive assembly 420 drives the withdrawal plate 410 to move closer to the delivery pipe 310, so that the next microchannel 100 can be sleeved on the joint 230. In addition to the withdrawal mechanism provided in this embodiment, other structures can also be used to separate the microchannel from the joint, for example, a claw is used to clamp the microchannel, and the claw is driven to pull the microchannel out of the joint to separate the two.

As a preferred implementation, in order to facilitate the assembly and disassembly of the microchannel 100, the outside of the fourth opening 232 of the joint 230 is in the shape of a circular truncated cone with a large upper diameter and a small lower diameter, to reduce the resistance for assembly and disassembly of the microchannel 100.

Specifically, the withdrawal plate driving assembly 420 comprises a withdrawal plate driving motor 421, a first screw 422, and a first screw nut 423, the withdrawal plate driving motor 421 is fixedly mounted on a mounting bracket 240, and an output end of the withdrawal plate driving motor 421 is connected with the first screw 422, the first screw nut 423 and the first screw 422 are fitting assembled, and the withdrawal plate 410 is connected with the first screw nut 423. The first screw nut 423 cooperates with the first screw 422 to convert the rotary motion output by the withdrawal driving motor 421 into a linear motion of the first screw nut 423 along the axial direction of the first screw 422, thereby bringing the withdrawal plate 410 to move linearly, of course, other types of linear driving assemblies can also be used to drive the withdrawal plate 410. For example, cylinder drive.

Figures 17, 18, 19:
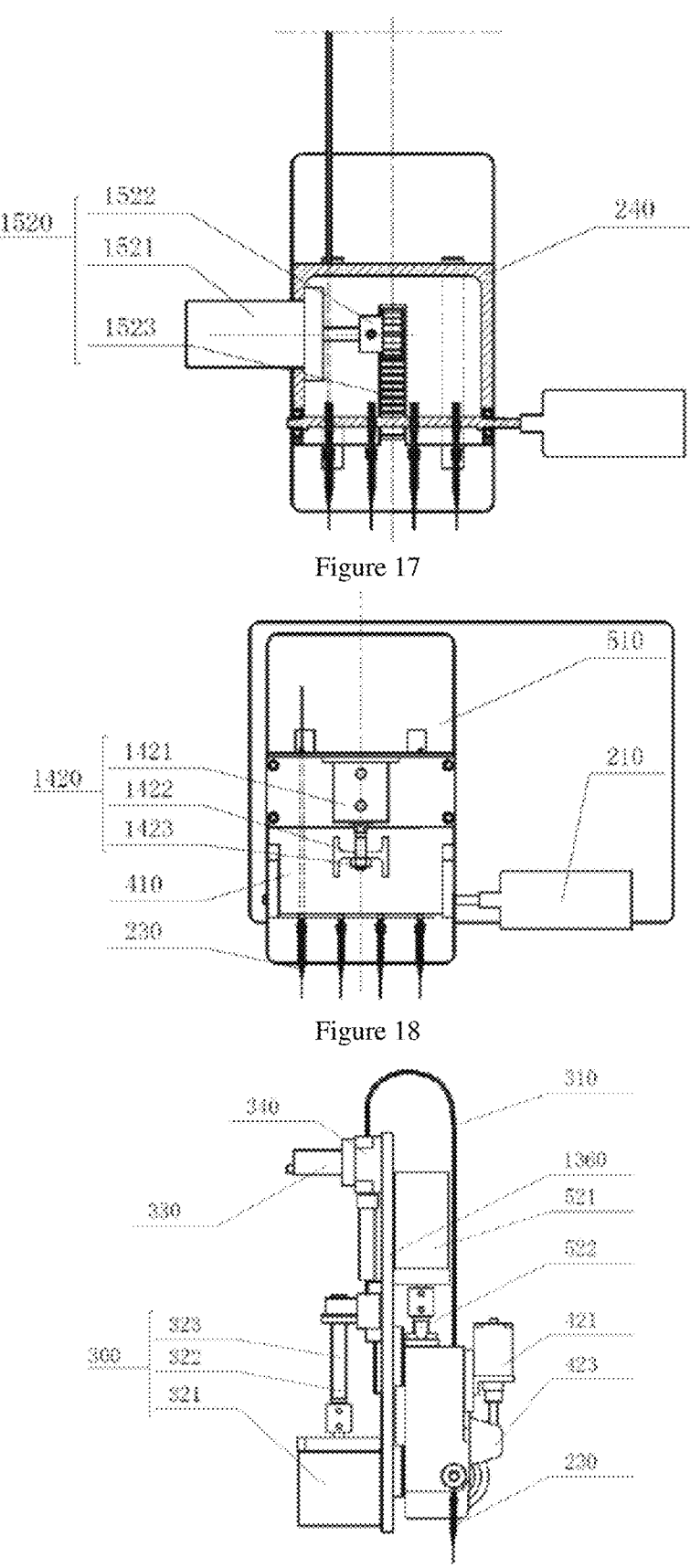
FIG. 17 is a front cross-sectional view of the micro-droplet generation device used in the another embodiment of the present disclosure.
FIG. 18 is a front view of the micro-droplet generation device used in the another embodiment of the present disclosure.
FIG. 19 is a left view of the micro-droplet generation device used in the another embodiment of the present disclosure.
Figure 20:
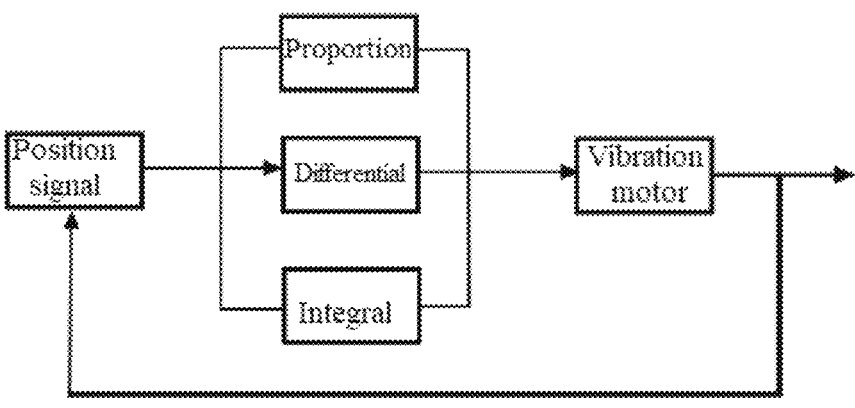
FIG. 20 is a schematic diagram of a motor for closed-loop control of the vibration angle or position involved in the micro-droplet generation device used in the present disclosure.

As shown in FIG. 18, another solution of the withdrawal plate driving assembly 420 comprises a first cylinder 1421 and a first fixing nut 1423, the first cylinder 1421 is fixedly mounted on a mounting bracket 240, the first fixing nut 1423 and a front end of a piston rod 1422 of the first cylinder 1421 are fitting assembled, and the withdrawal plate 410 is connected with the first fixing nut 1423. When gas is injected into the first cylinder 1421, the front end of the piston rod 1421 of the first cylinder stretch outward and moves along the axial direction of the piston rod. The first fixing nut 1423 cooperates with the front end of the piston rod of the first cylinder 1421 to transmit the axial movement output by the first cylinder 1421 to the withdrawal plate 410, so that the withdrawal plate 410 can be driven to move linearly to perform withdrawal.

Further, the rotation driving mechanism 200 further comprises a mounting bracket 240, the rotating motor 210 and the withdrawal plate driving motor 421 are respectively fixedly mounted on the mounting bracket 240, and both ends of the rotating shaft 220 are rotatably arranged in the mounting bracket 240 through bearings, so that he structure of the rotation driving mechanism 200 can be made more compact and stable.

Furthermore, as shown in FIG. 9, the micro-droplet generation device further comprises a longitudinal movement mechanism 500, the longitudinal movement mechanism 500 comprises a first mounting plate 510, a longitudinal movement driving assembly 520, and a longitudinal sliding assembly 530, the mounting bracket 240 is mounted on the first mounting plate 510 by the longitudinal sliding assembly 530, and the longitudinal movement driving assembly 520 is used to drive the mounting bracket 240 to slide along the longitudinal sliding assembly 530. Under the action of the longitudinal movement driving assembly 520, the mounting bracket 240 can drive the rotation driving mechanism 200 to move in the longitudinal direction, that is, the joint 230 on the rotating shaft 220 can move in the longitudinal direction. By controlling the joint 230 to move in the longitudinal direction, the microchannel 100 on the joint 230 can be driven to move synchronously in the longitudinal direction, and when the first opening of the microchannel 100 needs to be inserted below the second liquid surface, the longitudinal movement mechanism 500 can be controlled to drive the microchannel 100 to move down to a predetermined height; when the microchannel 100 needs to be moved out, the longitudinal movement mechanism 500 can be controlled to drive the microchannel 100 to move upward. The longitudinal movement mechanism 500 also provides conditions for the joint 230 to automatically load the microchannel 100, when the microchannel 100 needs to be mounted on the joint 230, the microchannel 100 can be placed below the joint 230 so as to align the second opening 120 of the microchannel 100 with the joint 230, start the longitudinal movement driving assembly 520, drive the connector 230 to move downward, insert the fourth opening 232 of the joint 230 into the second opening 120 of the microchannel 100, and then drive the joint 230 to move upward to return. In addition, after the microchannel 100 is loaded on the joint 230, the longitudinal movement driving assembly 520 can also drive the microchannel 100 to move downward so that the first opening 110 is inserted under the liquid surface of the second liquid 610, and reciprocating swings to produce micro-droplets.

Specifically, as shown in conjunction with FIG. 8 and FIG. 9, the longitudinal movement driving assembly 520 comprises a longitudinal movement driving motor 521, a second screw 522, and a second screw nut 523, the longitudinal movement driving motor 521 is fixedly mounted on a first mounting plate 510, and an output end of the longitudinal movement driving motor is connected with the second screw 522, the second screw nut 523 and the second screw 522 are fitting assembled, and the mounting bracket 240 is connected with the second screw nut 523. The second screw nut 523 cooperates with the second screw 522 to convert the rotary motion output by the longitudinal movement driving motor 521 to a linear motion of the second screw nut 523 along the axial direction of the second screw 522, thereby bringing the mounting bracket 240 to move linearly, of course, other types of linear driving assemblies can also be used to drive the mounting bracket 240. For example, rack drive.

As shown in FIG. 17, another solution of the longitudinal movement driving assembly 520 comprises a longitudinal movement gear driving motor 1521 with a power-off brake, a first gear 1522 and a first rack 1523, the longitudinal movement gear driving motor 1521 is fixedly mounted on the mounting bracket 240, an output end of the longitudinal movement driving motor is connected with the first gear 1522, the first rack 1523 is fixed on the first mounting plate 510, and the first rack 1523 and the first gear 1522 are fitting assembled. The first gear 1522 cooperates with the first rack 1523 to convert the rotary motion output by the longitudinal movement gear driving motor 1521 to a linear motion of the longitudinal movement gear driving motor 1521 and the first gear 1522 along the axial direction of the first rack 1523, thereby bringing the mounting bracket 240 to move linearly, of course, other types of linear driving assemblies can also be used to drive the mounting bracket 240.

Figure 11:
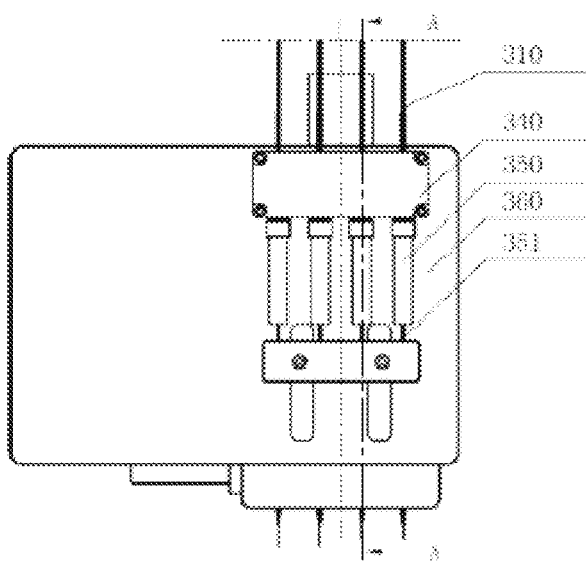
FIG. 11 is a rear view of the micro-droplet generation device of one embodiment.

As shown in FIG. 10, FIG. 11 and FIG. 12, the fluid driving mechanism 300 in this implementation comprises an injector 350 and an injector driving assembly 320, the liquid inlet and outlet of the injector 350 are in communication with the second opening 120 of the microchannel 100 through the delivery pipe 310. The push rod 351 of the injector 350 slides in the cylinder of the injector 350 under the drive of the injector driving assembly 320, and pushes the driving liquid therein to enter the microchannel 100 through the delivery pipe 310 and the joint 230, and then to provide fluid driving force to the first liquid 130 in the microchannel 100. The fluid driving mechanism provided by the present disclosure is not limited to the above-mentioned implementations, for example, a peristaltic pump, a pressure driving pump, a pneumatic driving pump, an electroosmotic driving pump, or the like can also be used.

Further, as shown in FIG. 12, the fluid driving mechanism 300 further comprises a three-way reversing valve 330 and a liquid storage tank, the second opening 120 of the microchannel 100, the liquid inlet and outlet of the injector 350, and the liquid outlet of the liquid storage tank are connected with three ports of the three-way reversing valve 330. The three-way reversing valve 330 can at least control the fluid driving mechanism 300 to achieve the following two modes: I. causing the liquid inlet and outlet of the injector 350 to be in communication with the second opening 120 of the microchannel 100, and driven by the injector driving assembly 320, the injector 350 provides the liquid driving force to the microchannel 100 for pushing the first liquid in the microchannel 100 from the first opening 110, or sucking the first liquid from the first opening 110 into the microchannel 100; II. causing the liquid inlet and outlet of the injector 350 to communicate with the liquid storage tank, and driven by the injector driving assembly 320, the injector 350 sucks the driving liquid in the liquid storage tank into the tube of the injector 350, or pushes the driving liquid in the injector 350 into the liquid storage tank.

As shown in FIG. 8, FIG. 9 and FIG. 11, in order to improve the efficiency of micro-droplet generation, as a preferred implementation, there is a pluralities of micro-channels 100, joints 230, delivery pipes 310, and injectors 350, the plurality of joints 230 are arranged at intervals on the rotating shaft 220, and the plurality of microchannels 100 are respectively mounted on the joints 230, two ends of each delivery pipe 310 are respectively in communication with the second opening of a microchannel 100 and a first port of the three-way reversing valve 330, the liquid inlet and outlet of each injector 350 are connected with a second port of the three-way reversing valve 330, and the liquid outlet of the liquid storage tank is connected with a third port of the three-way reversing valve 330. The plurality of microchannels 100 can be driven by the injector 350 and the rotating motor 210 to simultaneously perform the work of micro-droplet generation, and one three-way reversing valve 330 can simultaneously control the micro-droplet generation state of the plurality of microchannels 100.

As a preferred implementation, a plurality of three-way reversing valves 330 can also be provided corresponding to the plurality of microchannels 100, joints 230, delivery pipes 310, and injectors 350, and the plurality of three-way reversing valves 330 are respectively in communication with the plurality of delivery pipes 310 and the plurality of injectors 350, so that the plurality of three-way reversing valves can be independently controlled to achieve independent control of the micro-droplet generation state of the plurality of microchannels 100.

Figure 14:
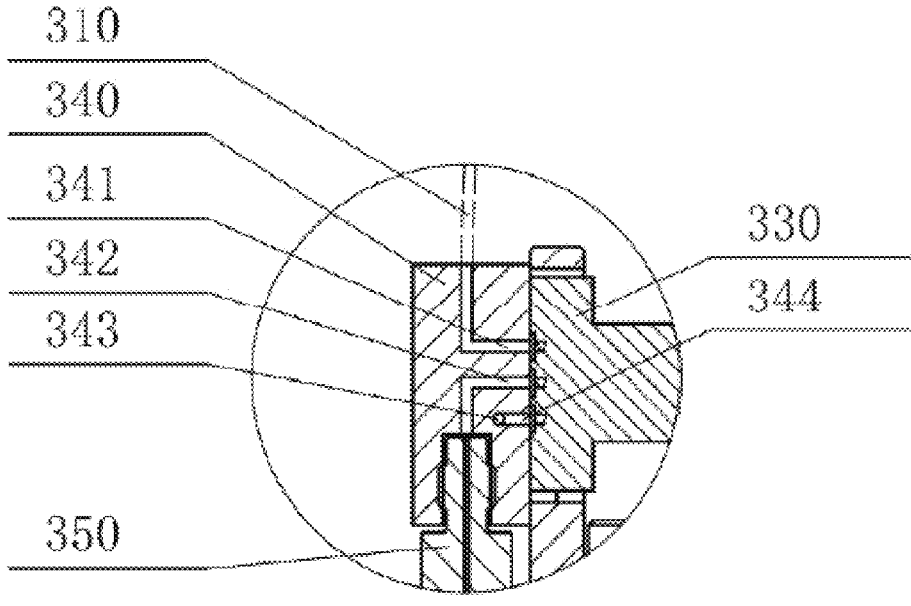
FIG. 14 is a partial enlarged view of Position D in FIG. 12.
Figure 15:
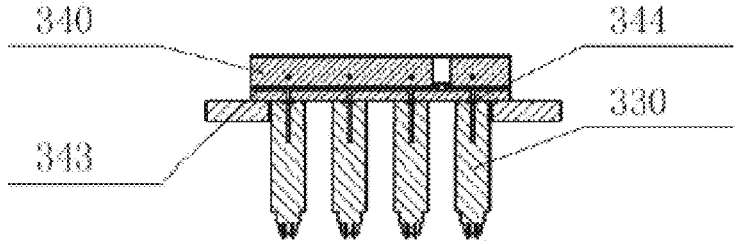
FIG. 15 is a cross-sectional view along B-B in FIG. 12.

Further, as shown in FIG. 12, FIG. 14 and FIG. 15, the fluid driving mechanism 300 further comprises a mounting block 340, the plurality of three-way reversing valves 330 and injectors 350 are fixedly mounted on the mounting block 340, and the mounting block 340 is provided with a plurality of first flow channels 341, a plurality of second flow channels 342, one third flow channel 343 and a plurality of liquid distribution channels 344, two ends of each first flow channel 341 are respectively in communication with one delivery pipe 310 and one first port of the three-way reversing valve 330, two ends of each second flow channel 342 are respectively in communication with the liquid inlet and outlet of one injector 350 and the second port of one three-way reversing valve 330, the third flow channel 343 is in communication with the liquid storage tank and the plurality of liquid distribution channels 344, and each liquid distribution channel 344 is in communication with the third port of one three-way reversing valve 330.

Specifically, as shown in FIG. 10, the injector driving assembly 320 comprises an injector driving motor 321, a third screw 322, and a third screw nut 323, an output end of the injector driving motor 321 is connected with the third screw 322, the third screw nut 323 and the third screw 322 are fitting assembled, and the push rods 351 of the plurality of injectors 350 is connected with the third screw nut 323 through connectors (not shown in the figure). The third screw nut 323 cooperates with the third screw 322 to convert the rotary motion output by the injector driving motor 321 into a linear motion of the third screw nut 323 along the axial direction of the third screw 322, thereby bringing the push rod 351 of the injector 350 to move linearly, of course, other types of linear driving assemblies can also be used to drive the push rod 351. For example, rack drive.

Figure 16:
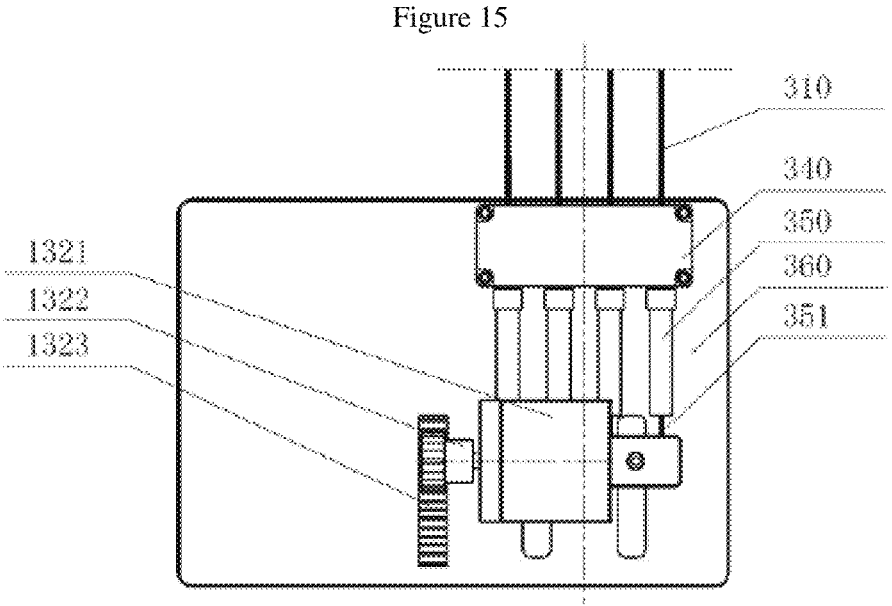
FIG. 16 is a rear view of the micro-droplet generation device used in another embodiment of the present disclosure.

As shown in FIG. 16, another solution of the injector driving assembly 320 comprises an injector gear driving motor 1321 with a power-off brake, a second gear 1322 and a second rack 1323, an output end of the injector driving motor 1321 is connected with the second gear 1322, the second rack 1323 is connected with the second mounting plate 360, the second rack 1323 and the second gear 1322 are fitting assembled, and the push rods 351 of the plurality of injectors 350 is connected with the injector gear driving motor 1321 through connectors (not shown in the figure). The second gear 1322 cooperates with the second rack 1323 to convert the rotary motion output by the injector gear driving motor 1321 to a linear motion of the injector gear driving motor 1321 and the second gear 1322 along the axial direction of the second rack 1323, thereby bringing 351 of the injectors 350 to move linearly, of course, other types of linear driving assemblies can also be used to drive the push rods 351.

More further, the fluid driving mechanism 300 further comprises a second mounting plate 360, the mounting block 340 and the injector drive motor 321 are fixedly mounted on the second mounting plate 360, so that the second mounting plate 360 makes the fluid driving mechanism 300 more compact and stable. At the same time, the first mounting plate and the second mounting plate can be combined to save space, for example, as shown in FIG. 19, the injector driving assembly 320 can be mounted on the integrated mounting plate 1360, and the rest of the mounting and driving modes are unchanged.

As a preferred embodiment, the rotating motor 210 can adopt a vibration motor, which can provide stable and high-speed reciprocating swing motion, and the swing amplitude and frequency can be set according to requirements, which greatly improves the application scope of the micro-droplet generating device. At the same time, the withdrawal plate driving motor 421, the longitudinal movement driving motor 521, and the injector driving motor 321 can adopt stepping motors, and the structure fitting of the stepping motor and the screw nut can accurately control the linear motion stroke and improve the degree of automation.

Preferably, the rotating motor 210 adopts a motor for closed-loop control of vibration angle or position, and the motor for closed-loop control of vibration angle or position drives the rotation driving mechanism 200 to reciprocating swing, thereby precisely controlling the swing trajectory of the microchannel 100, thereby further reducing the disturbance caused by the environment and the system. Another advantage of this method is that the system parameters can be adjusted so that the critical volume can be reached within one swing cycle (as indicated by the arrow in FIG. 7). This means that only one droplet is produced during each cycle of rotation. In this way, changes in droplet volume caused by fluctuations of various environmental factors will not accumulate in the next cycle. Therefore, droplets of uniform size can be generated in large batches. This is also an advantage that other published solutions for generating nanoliter/picoliter emulsified droplets through mechanical motion do not have.

The application of the motor for closed-loop control of vibration angle or position in the present disclosure will be explained below combining with FIG. 16. The motor for closed-loop control of the vibration angle or position comprises components such as an infrared position sensor, a control circuit, and a signal processing circuit. In the present disclosure, the infrared position sensor is mounted on the rotating shaft 220 of the rotation driving mechanism 200, and the position signal obtained by the infrared position sensor is fed back to the control circuit, the control circuit performs proportional, integral, and differential operations on the feedback position signal according to the principle of PID automation control, and combining with position feed-forward, speed loop, current loop and other signal processing circuits, realizes the precise control of the absolute position of the motor when it is moving. The use of the motor for closed-loop control of vibration angle or position can prevent other vibration motors from changing the vibration position caused by complex load environment changes, which is conducive to precise control of the droplet volume and generation speed in engineering.

In this implementation, a liquid storage cavity with a volume of 10 μL to 100 μL is formed between the first opening 110 and the second opening 120 of the microchannel 100, the liquid storage cavity can store a certain amount of the first liquid to ensure the first liquid is sufficient to generate the required number of micro-droplets, and at the same time, the liquid storage cavity can also prevent the first liquid from being sucked into the joint 230 and the delivery pipe 310 through the micro-pipe 100, ensuring that the system will not be contaminated by the sample.

Preferably, the microchannel 100 may be made of a non-rigid material and has certain flexibility. The certain flexibility means that the microchannel 100 can make the movement path of the first opening 110 of the microchannel 100 have a certain standing wave phenomenon under the driving of the rotation driving mechanism 200. The use of microchannels made of materials with a certain flexibility further reduces the disturbance to the liquid surface, makes the generation of droplets easier and more uniform, and further reduces the phenomenon of liquid fragmentation.

In this implementation, the microchannel 100 is made of polypropylene with low surface energy; the delivery pipe 310 is made of Teflon.

In an implementation, the inner diameter of the orifice of the first opening 110 of the microchannel 100 is 1 μm-250 μm, and more preferably, the inner diameter of the orifice of the first opening 110 of the microchannel 100 is 10 μm-100 μm.

Next, the structure and working principle of the digital PCR chip in the present disclosure will be described in detail with reference to the drawings and embodiments.

Figure 21:
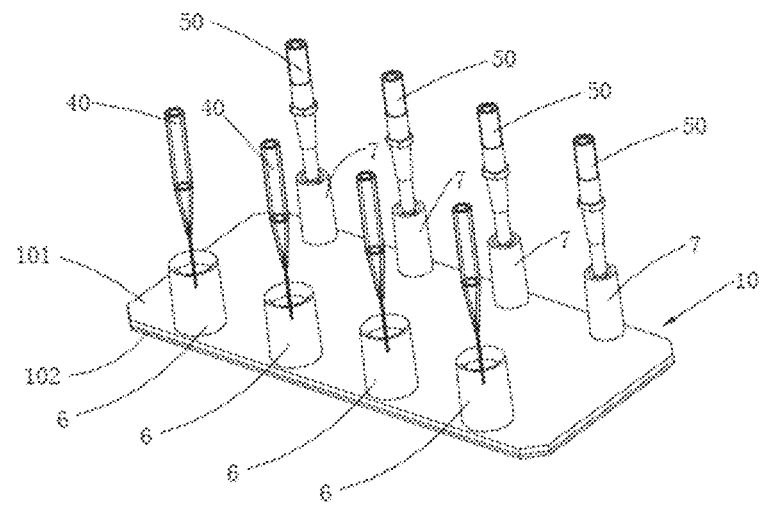
FIG. 21 is a schematic structure diagram of a digital PCR chip system of Embodiment 1 of the present disclosure.
Figure 22:
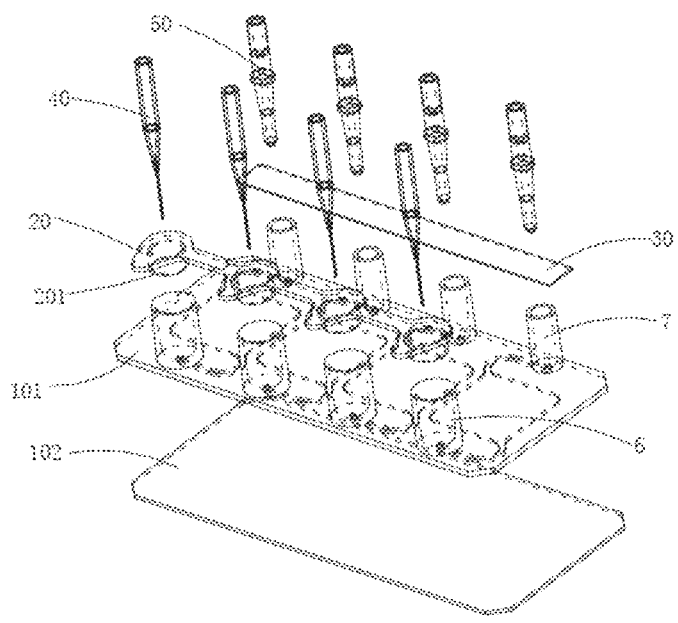
FIG. 22 is a schematic exploded structure diagram of the digital PCR chip system of Embodiment 1 of the present disclosure.
Figure 23:
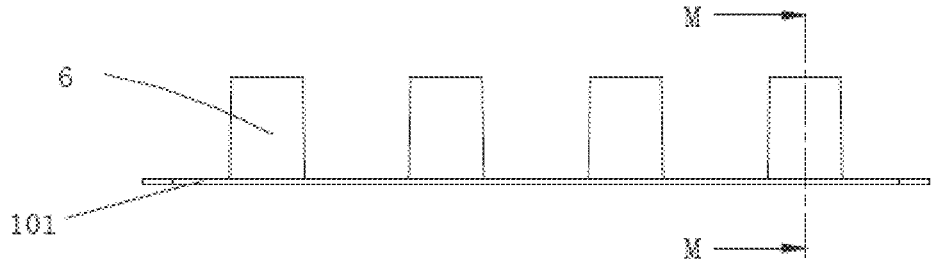
FIG. 23 is a front view of the chip substrate of the digital PCR chip of Embodiment 1.
Figure 24:
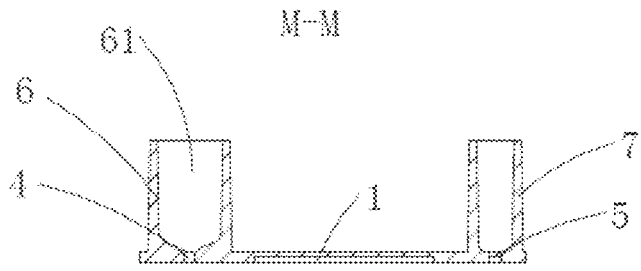
FIG. 24 is a schematic cross-sectional diagram along M-M direction in FIG. 23.
Figure 25:
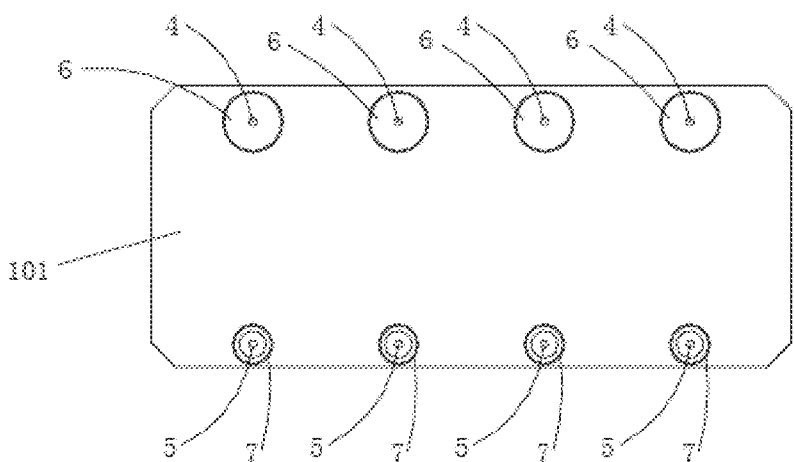
FIG. 25 is a top view of the chip body of FIG. 23.

Referring to FIG. 21 to FIG. 22, the digital PCR chip, the microchannel 100 of the present disclosure (also referred as the output gun needle in the present disclosure) and a negative pressure device for generating negative pressure and having a negative pressure gun needle 50.

The digital PCR chip of the present embodiment comprises a chip body 10 having a droplet storage cavity 1, a liquid inlet 4 and a liquid outlet 5 provided in the chip body 10, and a containing cavity 61 standing on the chip body 10 and being in communication with the liquid inlet 4, and the chip body 10 further comprises a first channel 2 enabling the liquid inlet 4 to be in communication with the droplet storage cavity 1, and a second channel 3 enabling the liquid outlet 5 to be in communication with the droplet storage cavity 1, wherein, the first channel 2 has a first internal pathway located inside the chip body 10, and the second channel 3 has a second internal pathway located inside the chip body 10.

In the digital PCR chip, the containing cavity 61 extends upward from the upper surface of the chip body 10, and the liquid inlet 4 is located at the bottom of the containing cavity 61. When in use, first fill the droplet storage cavity 1, the first channel 2, the second channel 3, and the containing cavity 61 with an oil phase, then inject a water phase into the oil phase in the containing cavity 61 by the output gun needle 40, and while injecting, reciprocating swing the output gun needle 40 to form droplets in the containing cavity 61. The density of the water phase is usually greater than that of the oil phase, and the formed droplets will deposit to the bottom of the containing cavity 61 due to their own gravity, and then enter the first channel 2 through the liquid inlet 4 to enter the droplet storage cavity 1.

Specifically, the containing cavity 61 has a length of 20 to 1000 μm, a width of 20 to 1000 μm, and a height of 20 to 2000 μm. The containing cavity 61 may be arranged to be fixedly connected to the chip body 10, or may be integrally formed with the chip body 10. In this embodiment, the upper surface of the chip body 10 has a liquid inlet diversion pipe 6 extending upright, and the pipe cavity of the liquid inlet diversion pipe 6 constitutes the above containing cavity 61.

In the digital PCR chip, one end portion of the second channel 3 is also connected to the droplet storage cavity 1. As preferably, in the digital PCR chip, on end portion of the first channel 2 is connected to the droplet storage cavity 1, and the first inner pathway is arranged on one side of the droplet storage cavity 1; one end portion of the second channel 3 is also connected to the droplet storage cavity 1, the second inner pathway and the first inner pathway are respectively provided on two different sides of the droplet storage cavity 1, and the negative pressure gun needle 50 of the negative pressure device can generate negative pressure through the liquid outlet, which assists the droplets to gradually enter the droplet storage cavity slowly from the first channel 2.

On the chip body 10, bottom surfaces of the first channel 2, the second channel 3, and the droplet storage cavity 1 are preferably arranged to be located at the same height, the height of the liquid inlet 4 in the vertical direction is higher than that of the first channel 2, and the height of the liquid outlet 5 in the vertical direction is higher than that of the second channel 3. The inner diameter of the liquid inlet 4 is preferably setted to 4 mm-8 mm, and the height is preferably 5 mm-15 mm. The inner diameters of the first channel 2 and the second channel 3 are respectively 4 mm-10 mm. The droplet storage cavity 1 has a length and width of 2-30 mm respectively, and a height of 20-2000 μm.

Figure 26:
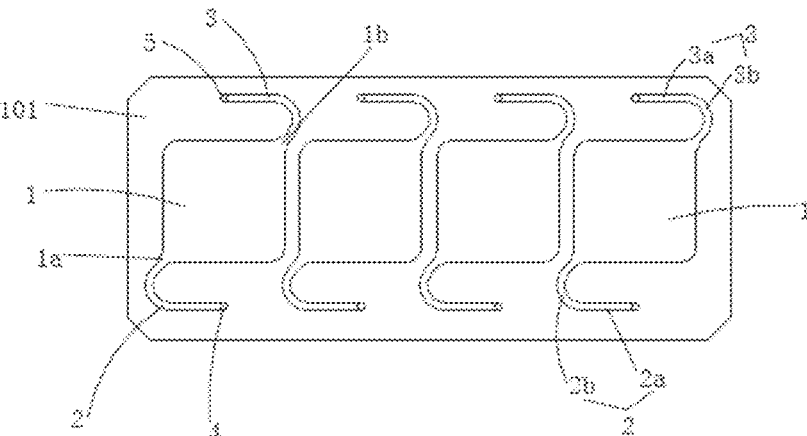
FIG. 26 is a bottom view of the chip body of FIG. 23.
Figure 27:
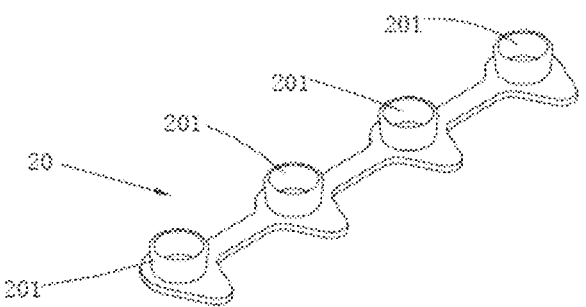
FIG. 27 is a schematic structure diagram of a sealing cover in the digital PCR system of Embodiment 1.
Figure 28:
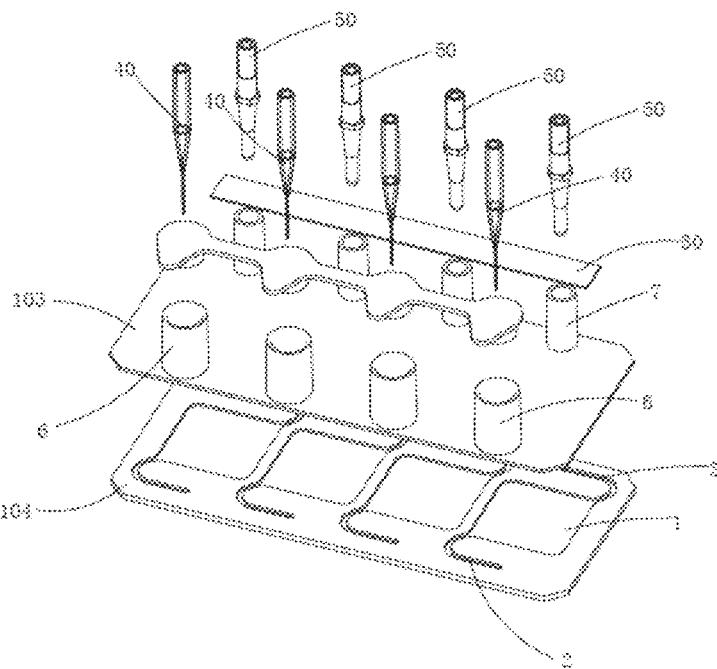
FIG. 28 is a first schematic exploded structure diagram of the digital PCR chip system of Embodiment 2 of the present disclosure.
Figure 29:
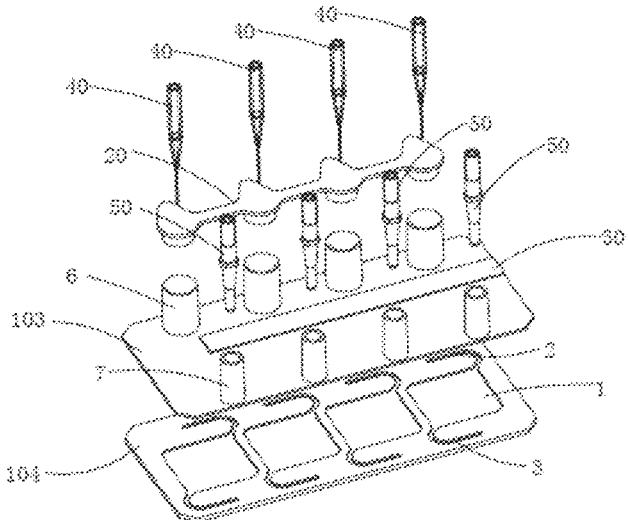
FIG. 29 is a second schematic exploded structure diagram of the digital PCR chip system of Embodiment 2 of the present disclosure.
Figure 30:
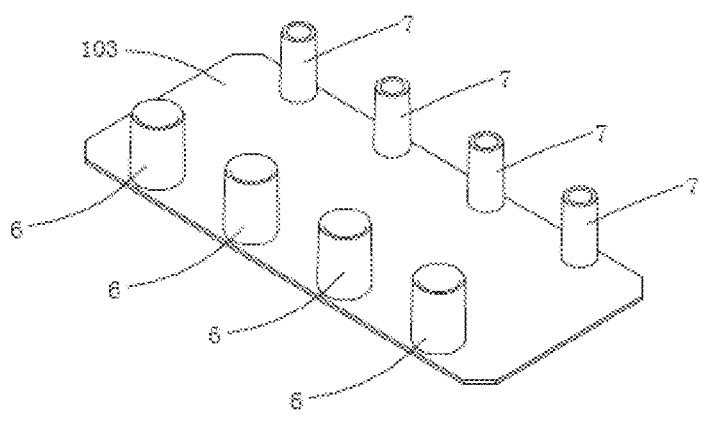
FIG. 30 is an isometric view of the chip cover in the digital PCR chip of Embodiment 2.
Figure 31:
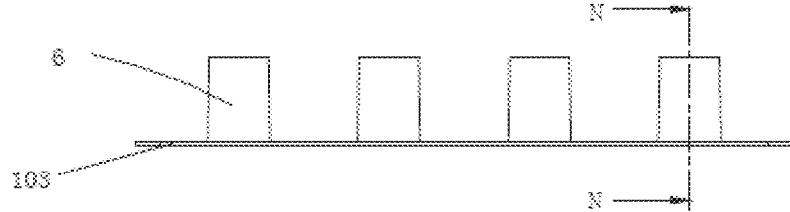
FIG. 31 is a front view of the chip cover plate of FIG. 30.
Figure 32:
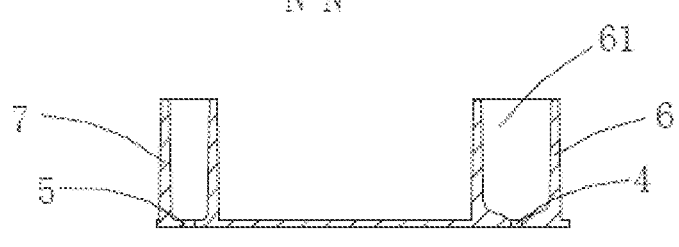
FIG. 32 is a schematic cross-sectional diagram along N-N direction in FIG. 31.
Figure 33:
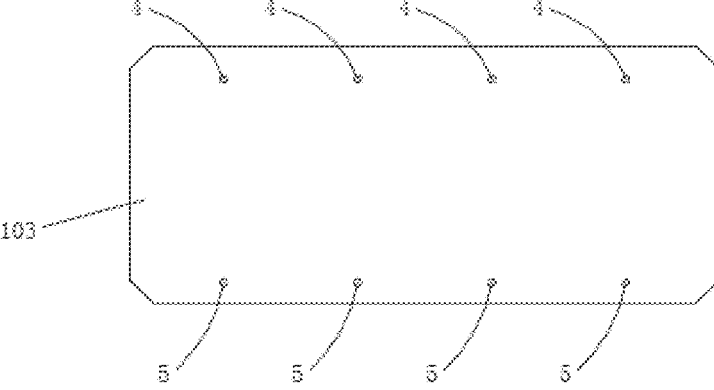
FIG. 33 is a bottom view of the chip cover plate of FIG. 30.
Figure 34:
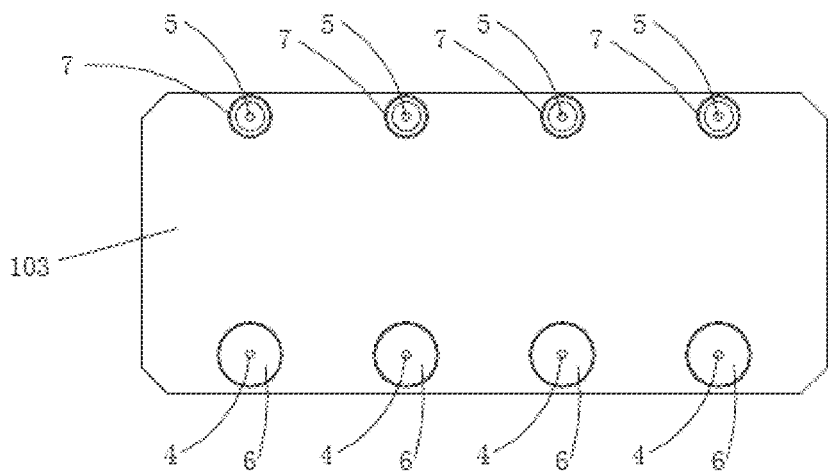
FIG. 34 is a top view of the chip cover plate of FIG. 30.
Figure 35:
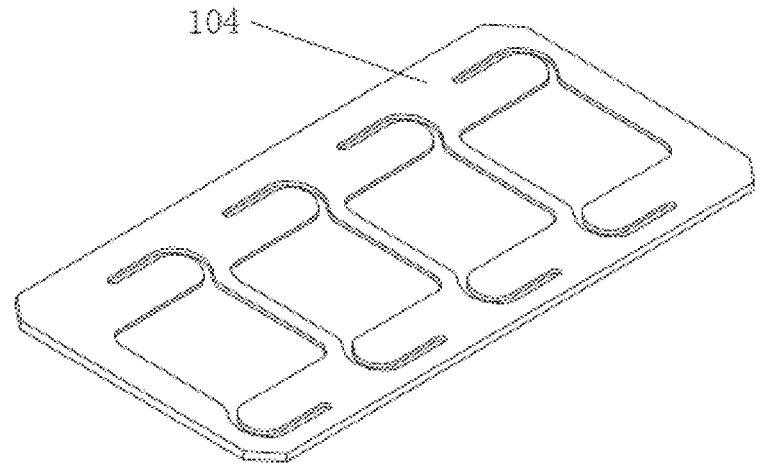
FIG. 35 is an isometric view of the chip substrate in the digital PCR chip of Embodiment 2.
Figure 36:
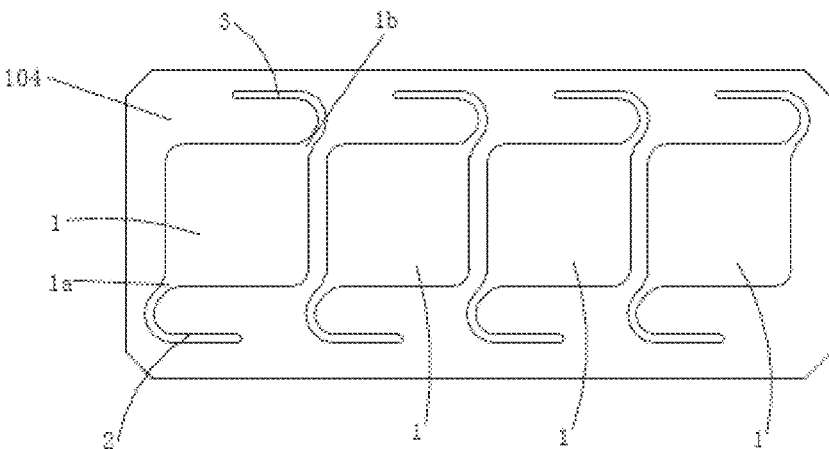
FIG. 36 is a top view of FIG. 35.

Referring to FIG. 26, the droplet storage chamber 1 has a first communication opening 1a being in communication with the first channel 2 and a second communication opening 1b being in communication with the second channel 3, and the first communication opening 1a and the second communication opening 1b are respectively arranged on two different sides of the droplet storage cavity 1, preferably the first communication opening 1a is arranged directly facing the second communication opening 1b; when the cross section of the droplet storage cavity 1 adopts a polygonal structure, the first communication opening 1a and the second communication opening 1b are preferably arranged on a group of opposite corners of the polygon.

In some embodiments, the droplet storage cavity 1 has at least one arc chamfer, and the first communication opening 1a is arranged at the arc chamfer, so that the first channel 2 is in communication with the first communication opening 1a and then is in communication with the droplet storage cavity 1, which is more conducive to achieve the tiling and movement of the droplets after entering the droplet storage cavity 1. The droplet storage cavity 1 may be a polygon having arc chamfers, or be circular or elliptical.

When the cross-section of the droplet storage cavity 1 is polygonal, the position where two adjacent edges meet can be used to form the above-mentioned arc chamfer, or one of the sides may be large chamfered to form the arc chamfer, and when the cross section of the droplet storage cavity 1 has other irregular shapes, it is better to perform large chamfering. As a preferred solution, in the cross section of the droplet storage cavity 1, the angle between at least two adjacent edges is a right angle, and the first communication opening 1a is provided at the right angle.

In this embodiment, the cross section of the droplet storage cavity 1 is arranged to be square, the first communication opening 1a and the second communication opening 1b are on a group of opposite corners, as shown in FIG. 26, the other inner corners are all arranged by inside arced chamfering, which is beneficial for the droplets to maintain good stability in the droplet storage cavity 1. The side length of the square cross section of the droplet storage cavity 1 is 5-30 mm, and the height of the droplet storage cavity 1 is 50-1000 μm. When the diameter of the droplet is reduced, the side length of the droplet storage cavity 1 can also be reduced to a smaller size, on the one hand, the height setting needs to meet the needs of droplet tiling, and on the other hand, it needs to take into account the issue of full utilization of formula oil.

As preferably, part or the whole of the first channel 2 and the second channel 3 are curved. In this embodiment, as shown in FIG. 26, the first channel 2 comprises a liquid inlet section 2a with one end being in communication with the liquid inlet 4, and a liquid outlet section 2b extending in an arc curve from the liquid inlet segment 2a toward the other end of the droplet storage cavity 1. The liquid inlet section 2a is a straight extension section, which is located outside the droplet storage cavity 1 and is parallel to one side of the droplet storage cavity 1, and one end of the liquid inlet section 2a is bent and extended toward the droplet storage cavity 1 to form the liquid outlet section 2b in an arc-shaped extension, the end portion of the liquid outlet section 2b away from the liquid inlet section 2a is connected to the first communication opening 1a and thus being in communicate with the droplet storage cavity 1, and this design is conducive to the droplet entering the first channel 2 via the liquid inlet 4 and smoothly entering the droplet storage cavity 1 under the action of gravity.

The second channel 3 and the first channel 2 are centrally symmetrically arranged. Specifically, the first channel 3 comprises a liquid outlet section 3a being in communication with the liquid outlet 5 at one end, and a liquid inlet section 2b extending in an arc curve from the liquid outlet segment 3a toward the other end of the droplet storage cavity 1, the liquid inlet section 3b is in an arc shape gradually arched away from the liquid outlet section 3a, and the end portion of the liquid inlet section 3b is connected to the second communication opening 1b and thus being in communicate with the droplet storage cavity 1.

On the whole, the first channel 2, the droplet storage cavity 1, and the second channel 3 form a centrally symmetric structure. This structure design realizes the smooth and steady delivery of the droplets and ensures the stability of the droplets.

The chip body 10 is mainly formed by superimposing a chip cover plate and a chip substrate in a thickness direction, the chip cover plate is a flat plate, a recess is provided on the chip substrate, and the flat plate and the recess are superimposed and compressed to form the droplet storage cavity 1, the first channel 2 and the second channel 3. In this embodiment, an opening of the recess faces downward, the chip substrate 101 is located above the chip cover plate 102, and the chip cover plate 102 is a transparent glass plate, a transparent PC plate, a transparent acrylic plate, a transparent COP plate or a black non-reflective plate made of non-reflective materials such as POM and PP. The chip substrate 101 and the chip cover plate 102 can be sealed by gluing, ultrasonic welding or thermal compression bonding processes, and the edges between the two should be absolutely sealed.

In another embodiment shown in FIG. 28 to FIG. 36, an opening of the recess faces upwards, and the chip substrate 104 is located below the chip cover plate 103, specifically, the liquid inlet 4 and the liquid outlet 5 are both opened on the chip cover plate 103, and the liquid inlet diversion pipe 6 and the liquid outlet diversion pipe 7 are also integrally formed on the chip cover plate 103; the droplet storage cavity 1, the first channel 2 and the second channel 3 are arranged on the chip substrate 104. The chip substrate 103 and the chip cover plate 104 mentioned above are both made of plastic, and can be welded to be sealed by the thermal compression bonding process.

Referring to FIG. 21, FIG. 22, FIG. 23, and FIG. 24, the upper surface of the chip body 10, that is, the upper surface of the chip substrate 101, further has a liquid outlet diversion pipe 7 extending upward and communicating with the liquid outlet 5, the liquid outlet diversion pipe 7 is mainly used as a negative pressure connector that is matched with the negative pressure gun needle 50, and the negative pressure gun needle 50 is matched with the liquid outlet diversion pipe 7 to form negative pressure on the droplet storage cavity 1. In this embodiment, the liquid inlet diversion pipe 6 and the liquid outlet diversion pipe 7 are integrally formed on the chip substrate 101, of course, in some other embodiments, they can also be formed using an independent processing method first and then connected to the chip substrate 101 by means of ultrasonic welding, glue bonding, or the like. The orifice of each liquid inlet diversion pipe 6 can be sealed by a detachable sealing cover 201, which is also to seal the containing cavity 61; the orifice of the liquid outlet diversion pipe 7 can be sealed by a sealing film 30.

Referring to FIG. 21 to FIG. 26, inside the chip body 10, the droplet storage cavity 1, the first channel 2 and the second channel 3 together constitute a chip unit, and the chip body 10 is provided with a plurality of above chip units arranged at intervals along the length direction, which can simultaneously carry out multiple sets of sample loading and analysis and detection. Correspondingly, pluralities of groups of liquid inlets 4, liquid outlets 5 and containing cavities 61 are also provided, and pluralities of groups of liquid inlet diversion pipes 6 and liquid outlet diversion pipes 7 are also provided. For the convenience of manufacturing and operation, all the sealing covers 201 adapted to the plurality of liquid inlet diversion pipes 6 are integrally arranged to form an integral sealing cover component 20, and the sealing film 30 is also used as an integral part and can simultaneously serve as a seal for the orifices of all liquid outlet diversion pipes 7.

The present disclosure further provides a detection method using a digital PCR chip or a digital PCR detection system as described above, which comprises a sample loading step of delivering droplets to the droplet storage cavity 1, and the sample loading step comprises:

filling the droplet storage cavity 1, the first channel 2, the second channel 3, and the containing cavity 61 of the digital PCR chip with an oil phase;

injecting a water phase into the oil phase in the containing cavity 61 by using a microchannel 100 (namely an output gun needle 40), and while injecting, reciprocating swinging the microchannel 100 to form droplets in the containing cavity 61;

delivering droplets to the droplet storage cavity 1 through the liquid inlet 4 and the first channel 2.

Wherein, before injecting the water phase, fully filling the droplet storage cavity 1, the first channel 2, and the second channel 3 with the oil phase. Before injecting the water phase, it is better to keep both the liquid inlet 4 and the liquid outlet 5 in a sealed state, and let the PCR chip to stand horizontally for more than 5 min; after starting to generate droplets or after completing droplet generation, the negative pressure device is switched on to promote the discharge of the oil phase from the liquid outlet 5 and to promote the flow of droplets to the droplet storage cavity 1.

Figures 37, 38, 39:
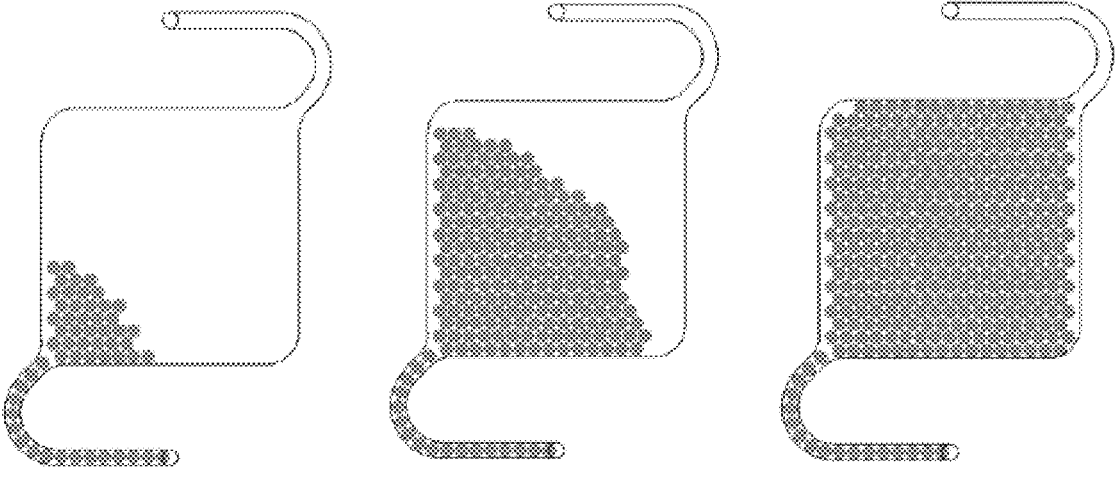
FIG. 37 to FIG. 39 are schematic diagrams showing that the droplets are tiled when the droplets enter the droplet storage cavity through the first channel.

The specific detection process is carried out according to the following steps: filling the droplet storage cavity 1, the first channel 2, the second channel 3, and the containing cavity 61 of the chip body 10 with an oil phase, and then sealing the orifices of the liquid inlet diversion pipe 6 and the liquid outlet diversion pipe 7 using the sealing cover 201 and sealing film 30. After the chip body 10 stands for more than 5 min, opening the sealing cover 201, inserting an output needle head of the output gun needle 40 of the droplet generation device into the containing cavity 61 of the liquid inlet diversion pipe 6, so that positioning the port of the output needle head (namely the first opening 110 of the microchannel 100) below the liquid surface of the oil phase and injecting the water phase, and while injecting, reciprocating swinging the output needle head to form droplets in the containing cavity 61. The generated droplets are accumulated at the bottom of the containing chamber 61 due to their own gravity, and some of the droplets naturally fall through the liquid inlet 4 to the first channel 2, and at this time, with the intervention of the droplets, the height of the oil phase will be increased in the liquid inlet 4, but it will not affect the stability of droplet generation. After completing the droplet generation, the sealing film 30 at the orifice of the liquid outlet diversion pipe 7 is pierced (an actionable mechanism matching with the instrument can be additionally provided to perform piercing), and the negative pressure gun needle 50 connected to the negative pressure device slowly generates negative pressure, and the droplets will slowly enter the droplet storage cavity 1 from the liquid inlet 4 through the first channel 2 under the action of pressure, and tile in a fan-shaped area to the droplet storage area 1, as shown in FIG. 37 to FIG. 39, the droplet generation and preliminary tiling process is completed at this time, and the chip body 10 can be pressed by a mechanical structure.

During the pressing process, it can be pressed on the upper surface of the whole chip body 10 or pressed at several fixed points, and the pressure is buffered by a structure such as a spring, and if several fixed points are used for pressing, it is necessary to avoid excitation light irradiation or camera detection light path area, so that real-time fluorescence reading can be performed, and the movement state of the droplets can be observed at any time.

Figures 40, 41, 42:
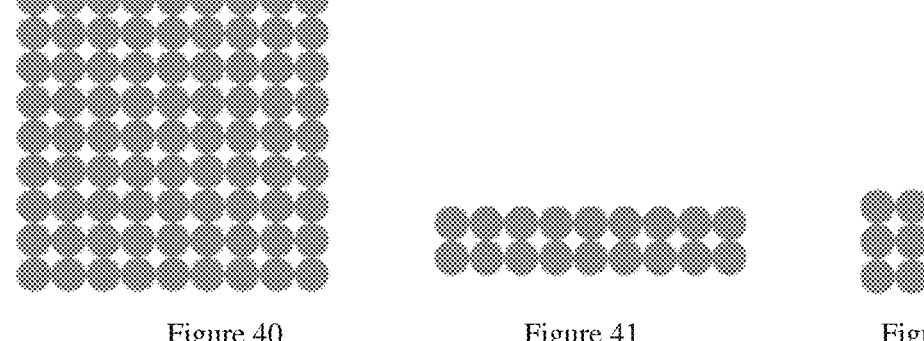
FIG. 40 is a schematic top view when the droplets are tiled in the droplet storage cavity.
FIGS. 41 and 42 are schematic diagrams when the droplets are tiled in two and three layers in the droplet storage cavity.

In addition, by adjusting the thickness and area of the droplet storage cavity 1, the volume of the droplet, and the total volume of the sample, one layer of tiling can accurately achieved, or two layers as shown in FIG. 41, or three layers as shown in FIG. 42, or even more layers. Assuming that the sample volume is 20 microliters, the droplet volume is 1 nanoliter, the chip area is 16 mm×16 mm, and the chip thickness is 125 to 150 micrometers, the generated 20,000 droplets can only be tiled in one layer. For the same sample volume of 20 microliters and a droplet volume of 1 nanoliter, if the chip area is adjusted to 11.5 mm×11.5 mm and the thickness is adjusted to 200 to 275 micrometers, 20,000 droplets can only be tiled in 2 layers.

This tiling method of multi-layer droplets can realize multi-layer observation of droplets with higher throughput per unit area. This is essential to improve the overall detection throughput of digital PCR equipment for image-based droplet detection, and solves the bottleneck problem of low detection throughput faced by such equipment.

The embodiments described above are only for illustrating the technical concepts and features of the present disclosure, and are intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A droplet generation system for digital PCR detection, comprising:

a PCR chip;

a microchannel comprising a water phase and having a first opening and a second opening for liquid to enter and exit;

a rotation driving mechanism for driving the microchannel to reciprocating swing; and a fluid driving mechanism for driving the liquid to pass through the microchannel;

wherein the PCR chip comprises:

a chip body having a droplet storage cavity, wherein a bottom surface of the droplet storage cavity is flat;

a containing cavity filled with oil standing on an upper surface of the chip body, wherein the microchannel is inserted into the containing cavity to inject the water phase into the oil such that droplets are generated within the containing cavity;

a liquid inlet having a height of 5 mm to 15 mm for the droplets generated within the containing cavity to enter into the droplet storage cavity, the liquid inlet being provided in the chip body and located at a bottom of the containing cavity; and a first channel connecting the liquid inlet to the droplet storage cavity, a liquid outlet provided in the chip body; and a second channel connecting the liquid outlet to the droplet storage cavity;

wherein, the first channel has a first internal pathway located inside the chip body, and the second channel has a second internal pathway located inside the chip body;

wherein the chip body comprises a chip cover plate that is a flat plate and a chip substrate having a recess, wherein the flat plate and the recess are superimposed and compressed to form the droplet storage cavity, the first channel and the second channel;

wherein the recess on the chip substrate comprises an opening that faces upward, the chip substrate is located below the chip cover plate, and the chip substrate and the chip cover plate are respectively made of plastic;

wherein a plurality of chip units are arranged on the chip body, and each chip unit of the plurality of chip units comprises the droplet storage cavity, the first channel, and the second channel;

a section of the droplet storage cavity is square or rectangular, a first communication opening and a second communication opening of the droplet storage cavity are respectively arranged at two opposite corners of the droplet storage cavity, the first internal pathway and the second internal pathway are respectively arranged on two opposite sides of the droplet storage cavity, the first communication opening is in communication with the first internal pathway, and the second communication opening is in communication with the second internal pathway;

the first internal pathway is formed by inner spaces of one straight extension section and one arc extension section, the straight extension section starting at the liquid inlet, which is located outside the droplet storage cavity, and extending from the liquid inlet parallel to one side of the droplet storage cavity, and one end of the straight extension section is bent and extended toward the droplet storage cavity to form the arc extension section, and an end portion of the arc extension section away from the straight extension section opens into the droplet storage cavity;

wherein droplets generated in the containing cavity deposit to a bottom of the containing cavity due to gravity and enter the first channel through the liquid inlet.

2. The droplet generation system according to claim 1, wherein a swing angle of the microchannel is 0.1° to 10°; and/or a frequency of the reciprocating swing of the microchannel is 1 Hz to 1000 Hz.

3. The droplet generation system according to claim 1, wherein the rotation driving mechanism comprises a rotating motor, a rotating shaft, and a joint, an output end of the rotating motor is connected with the rotating shaft, the joint is fixedly connected to the rotating shaft in a direction perpendicular to an axis of the rotating shaft, and the microchannel is detachably mounted on the joint.

4. The droplet generation system according to claim 3, wherein a plurality of joints is provided on the rotating shaft, and each of the plurality of joints is connected with a plurality of microchannels.

5. The droplet generation system according to claim 3, wherein the fluid driving mechanism comprises an injector and a delivery pipe, wherein the joint is tubular and comprises a first liquid inlet and outlet and a second liquid inlet and outlet being in communication with each other internally, wherein one end of the delivery pipe is connected to the liquid inlet and outlet of the injector, the other end is connected with the first liquid inlet and outlet of the joint, and an end of the microchannel where the second opening is located is connected with the second liquid inlet and outlet of the joint, wherein the fluid driving mechanism further comprises an injector driving assembly for driving the injector, the injector driving assembly comprising a lead screw nut driving mechanism or a rack and pinion driving mechanism, and wherein the droplet generation system further comprises a liquid storage tank with a liquid outlet, the liquid outlet of the liquid storage tank, the liquid inlet and outlet of the injector, and one end of the delivery pipe are connected via a three-way reversing valve.

6. The droplet generation system according to claim 3, wherein the droplet generation system further comprises a withdrawal mechanism for separating the microchannel from the joint.

7. The droplet generation system according to claim 6, wherein an end of the microchannel where the second opening is located is sleeved on one end portion of the joint, and the withdrawal mechanism comprises a withdrawal plate slidably arranged on the joint and a withdrawal plate driving assembly driving the withdrawal plate to slide, wherein the microchannel is separated from the joint by a sliding of the withdrawal plate against the microchannel, and wherein the withdrawal plate driving assembly is a lead screw nut driving structure or a cylinder driving structure.

8. The droplet generation system according to claim 1, wherein the droplet generation system further comprises a base frame, the rotation driving mechanism is arranged on the base frame in a manner of being capable of sliding up and down, and the droplet generation system further comprises a longitudinal movement driving mechanism that drives the rotation driving mechanism to slide.

9. The droplet generation system according to claim 1, wherein the rotation driving mechanism is detachably connected with the microchannel.

10. The droplet generation system according to claim 1, wherein the microchannel comprises a liquid storage cavity with a volume of 10 μL to 100 μL between the first opening and the second opening.

11. The droplet generation system according to claim 1, wherein the droplet generation system further comprises a drain pipe arranged on the chip body upright, wherein the drain pipe is in communication with the liquid outlet, the drain pipe extends upward from an upper surface of the chip body, and the drain pipe is integrally formed or fixedly connected with the chip body, wherein a negative pressure connector for mating with an outlet of a negative pressure device is provided on the liquid outlet, wherein the droplet generation system further comprises the negative pressure device for cooperating with the PCR chip to generate negative pressure in the first channel, the droplet storage cavity and the second channel, wherein the containing cavity extends upward from an upper surface of the chip body, and the liquid inlet is located at the bottom of the containing cavity, the containing cavity has a length of 2 mm to 30 mm, a width of 2 mm to 30 mm, and a height of 20 μm to 2000 μm, or the containing cavity and the chip body are integrally formed, or the containing cavity is fixedly connected with the chip body.

12. The droplet generation system according to claim 1, wherein one end portion of the first channel is in communication with the droplet storage cavity and/or one end portion of the second channel is in communication with the droplet storage cavity, wherein the first channel is located on one side of the droplet storage cavity and/or the second channel is located on one side of the droplet storage cavity.

13. The droplet generation system according to claim 1, wherein the first communication opening is arranged facing the second communication opening.

14. The droplet generation system according to claim 1, wherein a part or an entirety of the first channel and the second channel is curved, the first channel comprising at least one straight extension section and at least one arc extension section, and one end of the at least one straight extension section in communication with the liquid inlet, inner spaces of the at least one straight extension section, and the at least one arc extension section form the first internal pathway, the droplet storage cavity, the first channel, and the second channel form a centrally symmetric structure.

15. The droplet generation system according to claim 1, wherein bottom surfaces of the first channel, the second channel, and the droplet storage cavity are located at a same height, wherein a height of the liquid inlet in a vertical direction is higher than that of the first channel, and/or a height of the liquid outlet in the vertical direction is higher than that of the second channel, wherein the liquid inlet has an inner diameter of 4 mm to 8 mm, and/or the droplet storage cavity has a length and width of 2 mm to 30 mm, and a height of 20 μm to 1000 μm and/or the chip body has a thickness of 1 mm to 6 mm, or the chip further comprises a sealing cover for sealing the containing cavity, there is a plurality of containing cavities, and correspondingly, there is a plurality of sealing covers, and all of the plurality of sealing covers integrally arranged on an integral part.

16. The droplet generation system according to claim 1, wherein the chip cover plate is a transparent glass plate, a transparent PC plate, a transparent acrylic plate, a COP transparent plate or a black non-reflective plate.

17. A digital PCR detection method based on the droplet generation system according to claim 1, the droplets being formed by mixing the water phase and an oil phase, wherein the detection method comprises a sample loading step, and the sample loading step comprises:

filling the droplet storage cavity, the first channel, the second channel, and the containing cavity of the PCR chip with the oil phase;

inserting the first opening of the microchannel under a liquid surface of the oil phase in the containing cavity, initiating a rotating mechanism, driving the microchannel to reciprocating swing, and at a same time using the fluid driving mechanism and the microchannel to inject the water phase into the oil phase, to form droplets; and delivering droplets to the droplet storage cavity through the liquid inlet and the first channel.

18. The digital PCR detection method according to claim 17, wherein before injecting the water phase, fully filling the droplet storage cavity, the first channel, and the second channel with the oil phase, wherein after filling the oil phase and before injecting the water phase, keeping both the liquid inlet and the liquid outlet in a sealed state, and letting the PCR chip to stand horizontally for more than 5 min, wherein after starting to generate droplets, switching on a negative pressure device to promote a discharge of the oil phase from the liquid outlet and to promote a flow of droplets to the droplet storage cavity, wherein a swing angle of the microchannel is 0.1° to 10°, or wherein a frequency of the reciprocating swing of the microchannel is 1 Hz to 1000 Hz.

* * * * *